US007633621B2

(12) United States Patent
Thornton

(10) Patent No.: US 7,633,621 B2
(45) Date of Patent: *Dec. 15, 2009

(54) METHOD FOR MEASUREMENT OF ANALYTE CONCENTRATIONS AND SEMICONDUCTOR LASER-PUMPED, SMALL-CAVITY FIBER LASERS FOR SUCH MEASUREMENTS AND OTHER APPLICATIONS

(76) Inventor: Robert L. Thornton, 19 E. Portola Ave., Los Altos, CA (US) 94022

( * ) Notice: Subject to any disclaimer, the term of this patent is extended or adjusted under 35 U.S.C. 154(b) by 108 days.

This patent is subject to a terminal disclaimer.

(21) Appl. No.: 11/857,207

(22) Filed: Sep. 18, 2007

(65) Prior Publication Data

US 2008/0086038 A1 Apr. 10, 2008

Related U.S. Application Data

(63) Continuation-in-part of application No. 10/932,163, filed on Sep. 1, 2004, now Pat. No. 7,283,242, and a continuation-in-part of application No. 10/411,637, filed on Apr. 11, 2003, now Pat. No. 7,039,075, and a continuation-in-part of application No. 10/411,636, filed on Apr. 11, 2003, now Pat. No. 6,922,423.

(60) Provisional application No. 60/499,489, filed on Sep. 2, 2003.

(51) Int. Cl.
*G01N 21/00* (2006.01)
(52) U.S. Cl. ..................................... 356/432
(58) Field of Classification Search ............... 356/432; 72/26; 372/98, 22, 46
See application file for complete search history.

(56) References Cited

U.S. PATENT DOCUMENTS

| 4,523,279 A | 6/1985 | Sperinde et al. |
| 4,675,581 A | 6/1987 | Dietz |
| 4,680,767 A | 7/1987 | Hakimi et al. |

(Continued)

FOREIGN PATENT DOCUMENTS

EP 0119711 A1 2/1984

(Continued)

OTHER PUBLICATIONS

Baskin et al., "Accurate Characterization of Fiber Bragg Grating Index Modulation by Side Diffraction Technique", IEEE Photonics Technology Letters, vol. 15(3), pp. 449-451, Mar. 2003.

(Continued)

*Primary Examiner*—Tarifur R. Chowdhury
*Assistant Examiner*—Isiaka O Akanbi
(74) *Attorney, Agent, or Firm*—W. Douglas Carothers, Jr.; Carothers & Associates

(57) ABSTRACT

A hybrid laser comprising a semiconductor pump laser and small-cavity rare earth fiber laser where laser cavities of both lasers are butt coupled or otherwise optically coupled to form a plurality of laser cavities that produce a plurality of emission wavelengths, one which may be the pump laser emission wavelength at the output of the fiber laser thereby forming a multi-wavelength combined output. The wavelengths in such an output may substantially match distinguishing spectral characteristic features along at least a portion of a characteristic optical spectrum of the analyte under examination providing a method of determining the concentration of an analyte in a specimen undergoing examination.

15 Claims, 21 Drawing Sheets

U.S. PATENT DOCUMENTS

| | | | |
|---|---|---|---|
| 4,882,492 | A | 11/1989 | Schlager |
| 5,054,487 | A | 10/1991 | Clarke |
| 5,070,874 | A | 12/1991 | Barnes et al. |
| 5,267,152 | A | 11/1993 | Yang et al. |
| 5,348,003 | A | 9/1994 | Caro |
| 5,370,114 | A | 12/1994 | Wong et al. |
| 5,379,764 | A | 1/1995 | Barnes |
| 5,421,329 | A | 6/1995 | Casciani et al. |
| 5,424,545 | A | 6/1995 | Block et al. |
| 5,499,627 | A | 3/1996 | Steuer et al. |
| 5,553,613 | A | 9/1996 | Parker |
| 5,945,676 | A | 8/1999 | Khalil et al. |
| 5,946,085 | A | 8/1999 | Kawashima et al. |
| 5,966,392 | A * | 10/1999 | Chen et al. ............... 372/22 |
| 6,040,578 | A | 3/2000 | Malin et al. |
| 6,122,413 | A | 9/2000 | Jiang et al. |
| 6,137,812 | A | 10/2000 | Hsu et al. |
| 6,147,795 | A | 11/2000 | Derbyshire et al. |
| 6,185,230 | B1 | 2/2001 | Waarts |
| 6,205,164 | B1 | 3/2001 | Ohishi et al. |
| 6,236,047 | B1 | 5/2001 | Malin et al. |
| 6,263,002 | B1 | 7/2001 | Hsu et al. |
| 6,347,171 | B1 | 2/2002 | Tatah et al. |
| 6,549,861 | B1 | 4/2003 | Mark et al. |
| 6,560,381 | B2 | 5/2003 | Hatayama et al. |
| 6,570,893 | B1 | 5/2003 | Libatique et al. |
| 6,574,490 | B2 | 6/2003 | Abbink et al. |
| 6,587,704 | B1 | 7/2003 | Fine et al. |
| 6,628,696 | B2 * | 9/2003 | Thornton ............... 372/98 |
| 6,654,125 | B2 | 11/2003 | Maynard et al. |
| 6,671,528 | B2 | 12/2003 | Steuer et al. |
| 6,675,030 | B2 | 1/2004 | Ciurczak et al. |
| 6,684,099 | B2 | 1/2004 | Ridder et al. |
| 6,693,934 | B2 | 2/2004 | Wang |
| 6,717,972 | B2 | 4/2004 | Wolf et al. |
| 6,725,073 | B1 | 4/2004 | Motamedi et al. |
| 6,778,585 | B2 | 8/2004 | Malone |
| 6,795,478 | B2 * | 9/2004 | Hwang et al. ............... 372/96 |
| 6,798,810 | B2 | 9/2004 | Albrecht |
| 6,813,069 | B2 | 11/2004 | Rice et al. |
| 6,819,812 | B2 | 11/2004 | Kochergin et al. |
| 6,836,578 | B2 | 12/2004 | Kochergin et al. |
| 6,922,423 | B2 | 7/2005 | Thornton |
| 6,924,928 | B2 | 8/2005 | Dennis et al. |
| 6,993,221 | B2 | 1/2006 | Mihailov et al. |
| 7,031,571 | B2 | 4/2006 | Mihailov et al. |
| 7,039,075 | B2 | 5/2006 | Thornton |
| 7,113,524 | B2 | 9/2006 | Bonaccini et al. |
| 2002/0049372 | A1 | 4/2002 | Diab |
| 2002/0101904 | A1 | 8/2002 | Baillareon et al. |
| 2002/0159487 | A1 * | 10/2002 | Thornton et al. ............... 372/26 |
| 2003/0031221 | A1 | 2/2003 | Wang et al. |
| 2003/0112843 | A1 | 6/2003 | Thornton et al. |
| 2003/0235230 | A1 | 12/2003 | Thornton et al. |
| 2004/0028092 | A1 | 2/2004 | Kim |
| 2004/0184734 | A1 | 9/2004 | Mihailov et al. |
| 2004/0202400 | A1 | 10/2004 | Kochergin et al. |

FOREIGN PATENT DOCUMENTS

| | | |
|---|---|---|
| EP | 0899836 A1 | 3/1999 |
| WO | 0110294 A1 | 2/2001 |
| WO | 020229460 A1 | 4/2002 |
| WO | 02084826 A1 | 10/2002 |
| WO | 03007437 A2 | 1/2003 |
| WO | 03058781 A1 | 7/2003 |

OTHER PUBLICATIONS

Bernier et al., "Bragg Gratings Photoinduced in ZBLAN Fibers by Femtosecond Pulses at 800 nm", Optics Letters, vol. 32(5), pp. 454-456, Mar. 1, 2007.

Guillanume et al., "Monolithic Fluoride-Fiber Laser at 1460 nm Using Fiber Bragg Gratings", Optics Letters, vol. 32 (10), pp. 1302-1304, May 15, 207.

Wikszak et al., "Erbium Fiber Laser Based om Intracore Femtosecond-Written Fiber Bragg Grating", Optics Letters, vol. 31(16), pp. 2390-2392, Aug. 15, 2006.

Poignant et al., "Efficiency and Thermal Behavior of Cerium-Doped Fluorozirconate Glass Fiber Bragg Gratings", Electronic Letters, vol. 30(16), pp. 1339-1341, Aug. 4, 1994.

McAleavey et al., Narrow Linewidth, Tunable Tm3+-Doped..Gas Sensing, IEEE Journal of Selected Topics in Quantum Electronics, vol. 3(4), pp. 1103-1111, Aug. 1997.

Riley et al., "Matrix-Enhanced Calibration Procedure . . . Near-Infrared Spectra", Applied Spectroscopy, vol. 52(10), pp. 1339-1347, 1998.

McShane et al., "Improving Complex Near-IR Calibrations . . . Selection Algorithm", Applied Spectroscopy, vol. 53(12), pp. 1575-1581, 1999.

Ding et al., "Genetic Algorithm-Based Wavelength Selection . . . Effects of of Spectral Resolution", Analytical Chemistry, vol. 70(21), pp. 4472-4479, Nov. 1, 1998.

Caspary, "Applied Rare-Earth Spectroscopy for Fiber Laser Optimization", Dissertation, pp. 1-265 in pactular pp. 1-4, 29-34, 127-154 & 164-165, 2002.

Heise, "In Vivo Assay of Glucose", Biomedical Spectroscopy, Encyclopedia of Analytical Chemistry, Bimedical Spectroscopy, John Wilry & Sons, Ltd., Chichester, UK, pp. 56-83, 2000.

Khalil, "Spectroscopic and Clinical Aspects of Noninvasive Glucose Measurements"—Review, Clinical Chemistry, vol. 45(2), pp. 165-177 (1999).

Lu et al., "Multivariate Calibration Models . . . Single Beam Spectra", Applied Spectroscopy, vol. 51(9), pp. 1330-1399, 1997.

Marbach et al., "Optical Diffused Reflectance Accessory . . . Near-Infrared Spectroscopy", Applied Optics, vol. 34(4) pp. 610-621, Feb. 1, 1995.

Maruo et al., "Noninvasive Blood Glucose . . . Developed Near-Infrared System", IEEE Journal of Selected Topics in Quantum Electronics, vol. 9(2), pp. 322-330, Mar./Apr. 2003.

Mattu et al., "Application of Multivariate Calculation Techniques . . . Interferogram Data", Applied Spectroscopy, vol. 51 (9), pp. 1369-1376, 1997.

McShane et al., "Assessment of Partial Least-Squares Calibration . . . Near-Infrared Spectra", Applied Spectroscopy, vol. 52(6), pp. 878-884, 1998.

"Digital Lock-In Amplifiers—SK850"—Stanford Research Systems (Taken of Internet Site, Aug. 2004—5 Pages).

Ding et al., "Wavelength . . . Infrared Spectroscopy," AIP Conference Proceedings, Fourier Transform Spectroscopy, 11th International Conference Athens, GA, USA, pp. 264-267, 1998.

Hazen et al., "Temperature-Insensitive Near-Infrared Spectroscopic Measurement of Glucose in Aqueous Solutions," Applied Spectroscopy, vol. 48 pp. 477-483, 1994.

Heise et al., "Investigation of Experimental Errors . . . Human Blood Plasma by ATR-IR Spectroscopy," Journal of Molecular Structure, vol. 348, pp. 21-24, 1995.

Khalil, "Progress in Noninvasive Optical Diagnostics," Proceedings of the SPIE—The International Society for Optical Engineering, vol. 3913, pp. 2-14, 2000.

Percival et al., "Thulium-Doped Monomode Flouride Fibre Laser Broadly Tunable From 2.25 to 2.5 mm," Electronics Letters, vol. 27, pp. 1912-1913, 1991.

"About Lock-In Amplifiers, Application Note #3", Stanford Research Systems, (Taken of Internet Site, Aug. 2004—9 Pages).

Agger, "Single-Frequency Thulium-Doped Distributed-Feedback Fiber Laser", Optics Letters, vol. 29(13), pp. 1503-1505, Jul. 1, 2004.

Fieldler et al., "Design of VCSEL's for Feedback . . . Active Mode-Locking", IEEE Journal of Selected Topics on Quantum Electronics, vol. 1(2), pp. 442-444, Jun. 1995.

Olesberg et al., "In Vivo Near-Infrared . . . Blood Glucose Levels", Proceedings of SPIE, Diagnostics & Sensing IV, vol. 5325, pp. 11-20, Jun. 2004.

Horowitz et al., "The Art of Electronics" Second Eddition, pp. 774-776, Cambridge University Press, 1989.

Lorber et al., "Net Analyte Signal . . . Calibration", Analytical Chemistry, vol. 69(8), pp. 1620-1626, Apr. 15, 1997.

Yu et al., "Laser Diode Applications in Continous Blood Glucose Sensor", Proceedings of SPIE, vol. 4996, pp. 268-274, 2003.

Lee et al., "High Resolution Cryogenic Optical Fiber Sensor System Using Erbium-Doped Fiber", vol. 96(1), pp. 25-27, Jan. 31, 2002.

J. Schneider, "Mid-Infrared Fluoride Fiber Lasers in Multiple cascade Operation", IEEE Photonics Technology Letters, vol. 7(4), pp. 354-356, Apr. 1995.

Mihailov et al., "Bragg Gratings Written in All-SiO2 and Ge-Doped Core Fibers With 800-nm Femtosecond Radiation and a Phase mask", Journal of Lightwave Technology, vol. 22(1), pp. 94-100, Jan. 2004.

Percival et al., Highly Efficient CW Cascade Operation of 1.47 and 1.82 Micon Transitions in Tm-Doped Flouride Fibre Laser, Electronics Letters, vol. 28(20), pp. 1866-1868, Sep. 24, 1992.

Oi et al., "Fabrication of Fiber Bragg Grating by Femtosecond Laser Interferometry", pp. 776-777, 2001.

Smelser et al., "Operation of Pure Two-Beam Interference Grating Structures in an Optical Fiber With a Femtosecond Infrared Source and a Phase Mask", Optics Letters, vol. 29(15), pp. 1730-1732, Aug. 1, 2004.

* cited by examiner

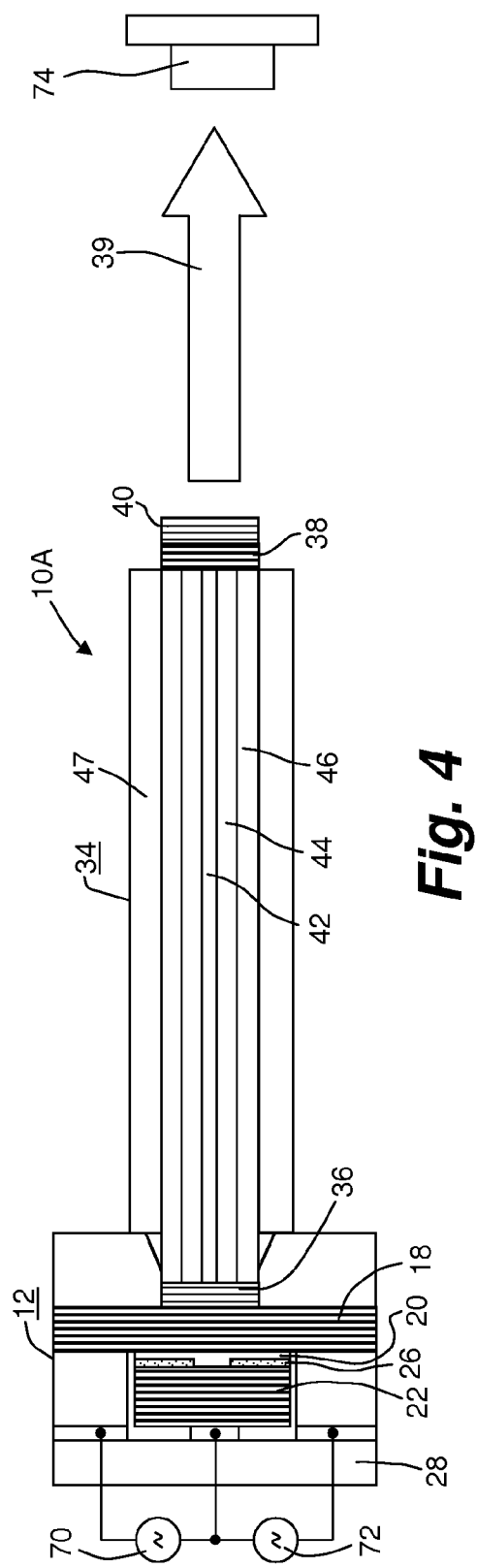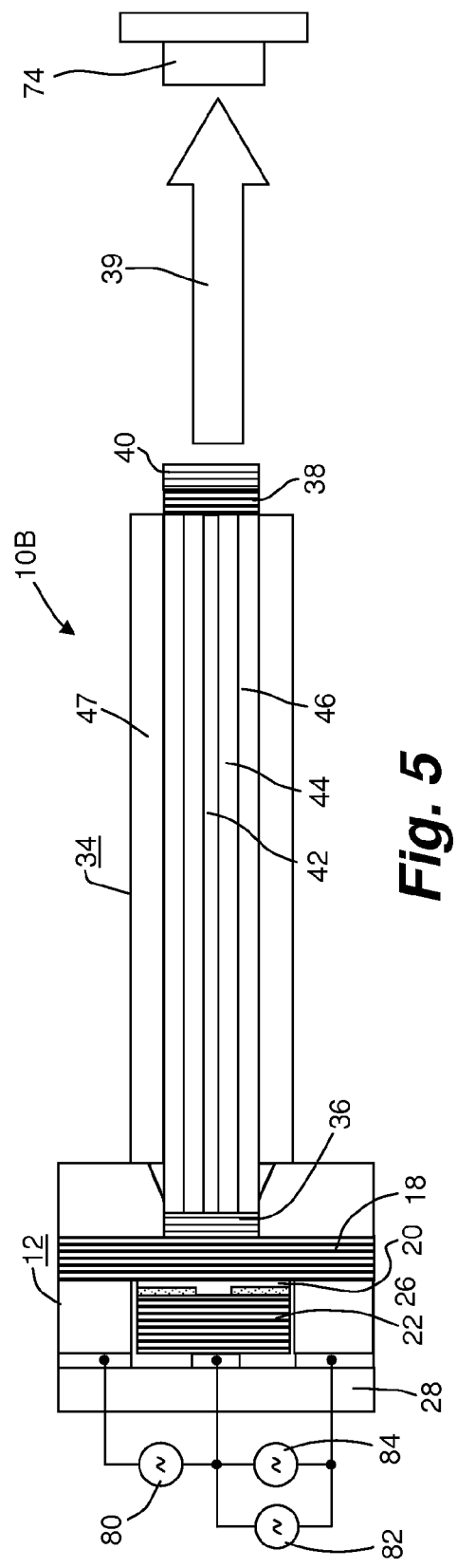

METHOD FOR MEASUREMENT OF ANALYTE CONCENTRATIONS AND SEMICONDUCTOR LASER-PUMPED, SMALL-CAVITY FIBER LASERS FOR SUCH MEASUREMENTS AND OTHER APPLICATIONS

REFERENCE TO RELATED APPLICATIONS

This application is a continuation-in-part of nonprovisional patent application, Ser. No. 10/932,163, filed Sep. 1, 2004 and entitled, OPTICAL SPECTROSCOPY APPARATUS AND METHOD FOR MEASUREMENT OF ANALYTE CONCENTRATIONS OR OTHER SUCH SPECIES IN A SPECIMEN EMPLOYING A SEMICONDUCTOR LASER-PUMPED, SMALL-CAVITY FIBER LASER, now U.S. Pat. No. 7,283,242, which claims priority to U.S. provisional application, Ser. No. 60/499,489, filed Sep. 2, 2003 and entitled, OPTICAL SPECTRAL ANALYSIS TECHNIQUE, and is a continuation-in-part of patent application, Ser. No. 10/411,637, filed Apr. 11, 2003 and entitled, FIBER EXTENDED, SEMICONDUCTOR LASER, now U.S. Pat. No. 7,039,075, and also is a continuation-in-part of patent application, Ser. No. 10/411,636, filed Apr. 11, 2003 and entitled, CONTROL SYSTEM FOR A SEMICONDUCTOR LASER, now U.S. Pat. No. 6,922,423, all of which applications are incorporated herein in their entirety by their reference.

BACKGROUND OF THE INVENTION

1. Field of Invention

This invention relates generally to optical spectroscopy and more particularly to the deployment of hybrid lasers comprising semiconductor-pumped, small- or micro-cavity fiber lasers having a wide operating spectrum that includes multiple wavelengths in the hybrid laser output that substantially match wavelength spectral characteristic features of analytes supporting the noninvasive measurement of analyte concentrations in a specimen analyte such as, for example, but not limited to, glucose, urea, alcohol, cholesterol or bilirubin in human tissue.

2. Description of the Related Art

Optical spectroscopy techniques are becoming increasingly important for a variety of applications for remote and non-invasive sensing. Within the medical health field, there is an extensive effort underway to develop the capability to non-invasively, and in real time, monitor the concentration of blood constituents, also referred to as analytes, such as alcohol, cholesterol, glucose, blood oxygen level or other such blood components. In particular, the ability to monitor the blood glucose concentration in a noninvasive manner would provide a tremendous benefit to the millions of people suffering from diabetes, which requires careful monitoring and control of blood glucose levels. Such a noninvasive approach is painless and does not require penetration of the skin to obtain or draw a blood sample. In order to perform the required spectroscopy to extract concentrations of blood constituents, current technology will typically use a broadband radiation source to illuminate the sample under test, either in-vivo or in-vitro, and couple radiation transmitted through or backscattered from the sample into an optical spectroscopy unit in order to extract information about the chemical composition of the illuminated material. Such a system is shown, for example, in U.S. pat. No. 6,574,490 and the references cited and discussed in that patent. Also mentioned in patent '490 are infrared spectroscopy methods employing infrared radiation either in an absorption mode or a reflective mode relative to analyte sample under examination. As a particular example, analytes, such as glucose, cholesterol, alcohol or oxygen content in the blood, will absorb differently, relative to absorption coefficient across the infrared spectrum. Since there are many different kinds of identifiable analytes in the sample, their absorption characteristics will overlap and vary differently from one another across the infrared spectrum and beyond such that there is no real reliable way to determine one analyte from another without some way of focusing, for example, on distinguishing intensities as wavelength spectral characteristic features along the characteristic optical spectrum of the analyte. However, how to accomplish, in a successful manner, the differential determination of these spectrum differences relative to one analyte over another in a sample in quick and simple way has eluded many of those skilled in the optical spectroscopy art, particularly since any system employed would have to successfully evaluate a plurality of intensities for a particular analyte to successfully achieve a reliably accurate measurement and final determination of its concentration on a continuous and speedy basis. Also, conventional infrared absorption spectroscopy is hampered by the intrinsic background absorption of water in the infrared spectrum that has strong absorption at spectral characteristic features of similar spectral characteristic features of a blood analyte. Water is nearly 95% of the human body. For example, glucose as an analyte has absorption spectrum peaks in the range of about 1,800 nm to 3,400 nm. But water also has a high and varying absorbance in this region and, therefore, can represent a constant and serious interference in determining the concentration of glucose in an in vivo specimen. Consequently it is very challenging to extract accurate measurements of the concentration of a specific blood analyte in the presence of interferences both from varying concentrations of other blood analytes and the strong and dominant absorption due to the presence of water. In summary, the optical spectroscopy art has yet to fully realize a low cost, noninvasive, highly portable analyte sensor which has the clinical accuracy required for widespread adoption.

The above mentioned prior art approaches are also cumbersome resulting in large and relatively inefficient measuring systems. The employment of a white light source consumes considerable power, much of which is not in the spectral ranges of interest. The spectrometer is inherently a large device with complex mechanical, or at best electro-optical, mechanisms that are sensitive to ambient conditions and poorly suited to applications where monitoring is desired in small clinics, homes, or as a small portable or wearable unit.

Thus, there is need for a noninvasive optical spectrometer system that provides for a compact and portable unit, such a palm unit, that will illuminate a subject sample or analyte at a signal set of pre-determined absorption wavelength features, collect these radiation signals from the result of scattering, reflection and/or absorption by the analyte to be analyzed, and provide for the precise determination of the relative strengths of the various spectral components of the collected signals relative to their respective initial signal strengths prior to impinging on the analyte. Therefore, there is further need for an effective radiation source that can provide multiple wavelength signals all sensitive to distinguishing wavelength spectral characteristic features, such as intensities of an analyte across a wide absorbance spectrum, which is also sufficiently compact and versatile to be of pocket size or employed in an in vitro manner or embedded in an in vivo manner. There is a further need for such a device to be based on a set of technologies that are capable of being readily manufactured at low cost and providing medically high reliability on a repeated basis of use.

SUMMARY OF THE INVENTION

According to this disclosure, a multi-cavity laser having a multi-wavelength output at one end, comprising a semiconductor pump laser optically coupled to a short cavity fiber laser having a rare earth doped core, the multi-cavity laser having a first resonator cavity formed by the laser cavities of the semiconductor laser and the fiber laser via a first mirror at one end of the semiconductor laser cavity and a mirror at the one end and at least one second resonator cavity formed in the fiber laser cavity with, respectively, a second and third mirror at each end of the fiber lasing cavity forming the second resonator cavity, where the first, second and third mirrors are fiber Bragg gratings.

An optical spectroscopy apparatus is also disclosed that may be employed to determine the concentration of analyte in a specimen that utilizes a single radiation source which is hybrid laser comprising a semiconductor pump laser and small-cavity rare earth fiber laser doped with a rare earth species where laser cavities of both lasers are butt coupled or otherwise optically coupled to form a plurality of laser cavities that produce a plurality of emission wavelengths, one which may be the pump laser emission wavelength at the output of the fiber laser, thereby forming a multi-wavelength combined output, where the wavelengths substantially match distinguishing spectral characteristic features along at least a portion of a characteristic optical spectrum of the analyte under examination. In lieu of complex data analysis of these wavelengths to determine values representing the concentration of the analyte in an examined specimen, the semiconductor pump laser or lasers are modulated as a plurality of tone frequencies, where at least a first of the modulation frequencies is below the maximum frequency response of the fiber laser so that the first modulation effectively modulates the pump emission wavelength and a first emission wavelength of the fiber laser in the hybrid laser combined output, and at least a second of modulation frequencies is above the maximum frequency response of the fiber laser so that the second modulation effectively modulates the pump emission wavelength but not the first emission wavelength of the fiber laser in the hybrid laser combined output. Further, one or more additional modulation frequencies may be applied to the pump laser which are intermediate of the first and second modulation frequencies where it is at least responsive to at least one further emission wavelength of the fiber laser and also provided in the hybrid laser combined output.

A further feature of this invention is the employment of a hybrid laser device comprising a semiconductor pump laser and a small- or micro-cavity fiber laser that are butt coupled, tightly coupled, or approximately coupled where the pump laser is the pumping source for the fiber laser that emits at it output one or more wavelengths as determined by the fiber laser cavity mirrors as well as may also emit at the pumping wavelength where the fiber laser cavity becomes a second laser cavity for the semiconductor pump laser by the deployment of an additional mirror or reflector at the end of fiber laser set to the pump wavelength. A key benefit of the foregoing laser geometry is that by placing the rare earth fiber into an extended version of the semiconductor laser cavity, the fiber laser optical cavity becomes a resonator at the semiconductor pump laser wavelength. This pump wavelength resonance serves to greatly increase the absorption efficiency of the pump laser radiation in the fiber laser optical cavity while maintaining a short physical path length in order to realize a compact laser. This allows relatively weak fiber absorption, such as in the case of an erbium doped fiber, to be more effectively and efficiently utilized in this hybrid laser geometry. The semiconductor laser may be a surface emitter laser or VCSEL laser and may also be an edge emitter laser. The planar fabrication process for the VCSEL pump laser readily lends itself to cost effective hybrid integration of arrays of such pump lasers, whether linear laser arrays or two-dimensional laser arrays, coupled with corresponding rare doped fiber lasers each having a doped fiber core with one or more rare earth materials, such as, for example, thulium, erbium, holmium, ytterbium, neodymium, promethium, terbium, praseodymium, or the like, to produce compact and efficient multi-wavelength radiation source modules for optical spectroscopy or other applications, for example, but not limited to, LIDAR. By appropriate design and electronic control of these modules, dramatic reductions in size and cost can be achieved for systems requiring precision wavelength, low noise optical spectroscopy.

It should be further noted, as alluded to just above, in arrays of such hybrid semiconductor pump lasers/fiber lasers, the cores of each of the fiber lasers in an array can contain all the same rare earth dopant, or different rare earth dopants or combinations of a plurality of different rare earth dopants. Thus, the novel semiconductor laser/fiber laser array of this invention enables compact, reliable radiation sources which span a broad combined range of fiber laser wavelengths and semiconductor laser wavelengths and able to accommodate compact multi-wavelength sources comprising 4 to 20 or more emission wavelengths from their hybrid laser outputs.

These multi-wavelength radiation sources can be targeted for emission within specific wavelength bands and at specific absorption peaks or other types of optical characteristic features, such as peaks in spectral residuals, that yield optimum spectral information on a targeted analyte or other organic or biotissue as well as targeted for power levels and modulation characteristics that enable the achievement of high signal to noise (SNR) spectral analysis. As an example of such targeted analyte or other organic or biotissue, specific examples are reference to the content of analytes in the blood, such as, glucose, oxygen content, alcohol, ethanol, albumin, urea, lactose and cholesterol.

A further feature of this invention is a noninvasive spectroscopic blood assay system for the quantitative assessment and measurement of human blood species, exemplified in the paragraph above, based upon an innovative laser technology platform that provides for a compact, portable and/or wearable ultra-high resolution, near-infrared, multi-wavelength spectroscopy system. This platform results in a major advanced noninvasive monitoring capability for patients requiring continuous monitoring of one or more blood analytes. As an example, in the case of glucose, diabetic sufferers are able to achieve continual, real-time monitoring of blood glucose levels in order to optimize disease management. Further, the platform is capable of cost effective production in large quantity in order to provide a reasonably priced unit for diabetic patients as end users of such units. For example, the size of such an unit, including its control electronics, is about the size of a cellular telephone with the capability of providing either on demand noninvasive sensing and monitoring or continuous noninvasive sensing and monitoring of the blood concentration of specific species or a specific set of blood species, such as, for example, glucose, cholesterol and alcohol, where the latter can have a significant affect on the maintenance of proper glucose and cholesterol levels in the body when the blood alcohol content is too high.

Another feature of this invention relates to optical spectroscopy apparatus for determining the concentration of an analyte in a specimen employing a hybrid laser that includes a semiconductor pump laser with a small-cavity fiber laser having a plurality of laser cavities that provide at an output from the hybrid laser a plurality of different emission wavelengths of radiation at least one from the small-cavity fiber laser and another from the semiconductor pump laser that substantially overlap distinguishing wavelength spectral characteristic features along at least a portion of a characteristic optical spectrum of the analyte; means for modulating the hybrid laser with a plurality of tone frequencies where all the tone frequencies effectively modulate an emission wavelength from the semiconductor laser and at least one tone frequency effectively modulates an emission wavelength from the fiber laser; means for collecting the modulated radiation from the hybrid laser output reflected from or passed through the specimen containing the analyte under examination; means for sensing the modulated tone frequencies from the collected radiation wavelengths producing a plurality of tone frequencies representative of values at the wavelength spectral characteristic features of the analyte within the characteristic optical spectrum portion; means for comparing the sensed tone frequencies with a set of corresponding tone frequencies absent of the spectral characteristic features from the analyte producing a set of values representative of spectral characteristic features after engagement with the analyte; and means for correlating differences in the set of values to produce a final value representative of a measurement of concentration of the analyte in the specimen.

It is within the scope of this invention that the claimed optical spectroscopy apparatus may also be employed as an in vivo means to determine, on a continuous basis, the concentration of a targeted analyte in the human body.

Other objects and attainments together with a fuller understanding of the invention will become apparent and appreciated by referring to the following description and claims taken in conjunction with the accompanying drawings.

BRIEF DESCRIPTION OF THE DRAWINGS

In the drawings wherein like reference symbols refer to like parts:

FIG. 4 is a cross-section view similar to FIG. 1 and where micro fiber laser is modulated with multiple frequency signals comprising two different frequencies.

FIG. 5 is a cross-section view similar to FIG. 1 and where micro fiber laser is modulated with multiple frequency signals comprising three different frequencies.

DETAILED DESCRIPTION OF THE INVENTION

As used herein, "small cavity" fiber laser means a comparatively very small laser cavity compared to fiber lengths generally employed for fiber lasers in the art. Typical fiber lengths for the VCSEL-pumped small cavity fiber laser employed in this invention may lie in the range, for example, from about 0.5 cm to about 10 cm, although the fiber length may also lie outside this range. The concentration for the dopant species may be in the range from 1,000 ppm to 30,000 ppm and typical inner core diameters of the fibers may be in the range from about 3 µm to about 10 µm, although it will be appreciated that the dopant concentration and the fiber core diameter may also lie outside these ranges. Also, as used herein, "spectral characteristic feature" means a minimum, zero or maximum of wavelength variation of an optical characteristic along at least a portion of the characteristic optical spectrum of an analyte under examination. An optical characteristic feature may include absorption, transmission or scattering independently, or a difference in any of these characteristics relative to any given set of reference or interfering optical characteristics. Examples of such sets are net analyte signal (NAS) and spectral residuals.

Figure 1:
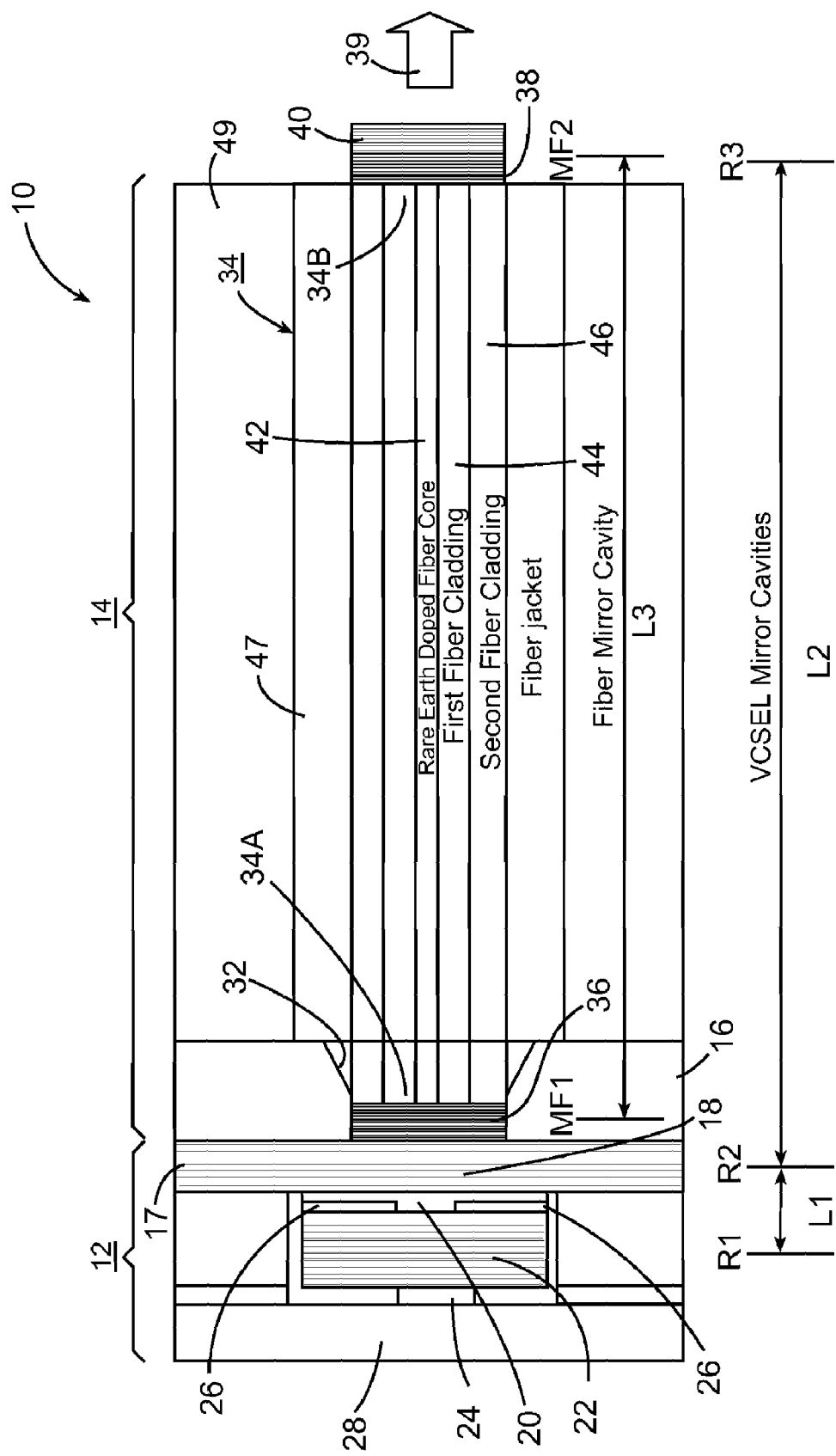
FIG. 1 is a cross-sectional side elevation view of a VCSEL or surface emitter pumped micro fiber laser adapted for deployment in this invention.
Figure 2:
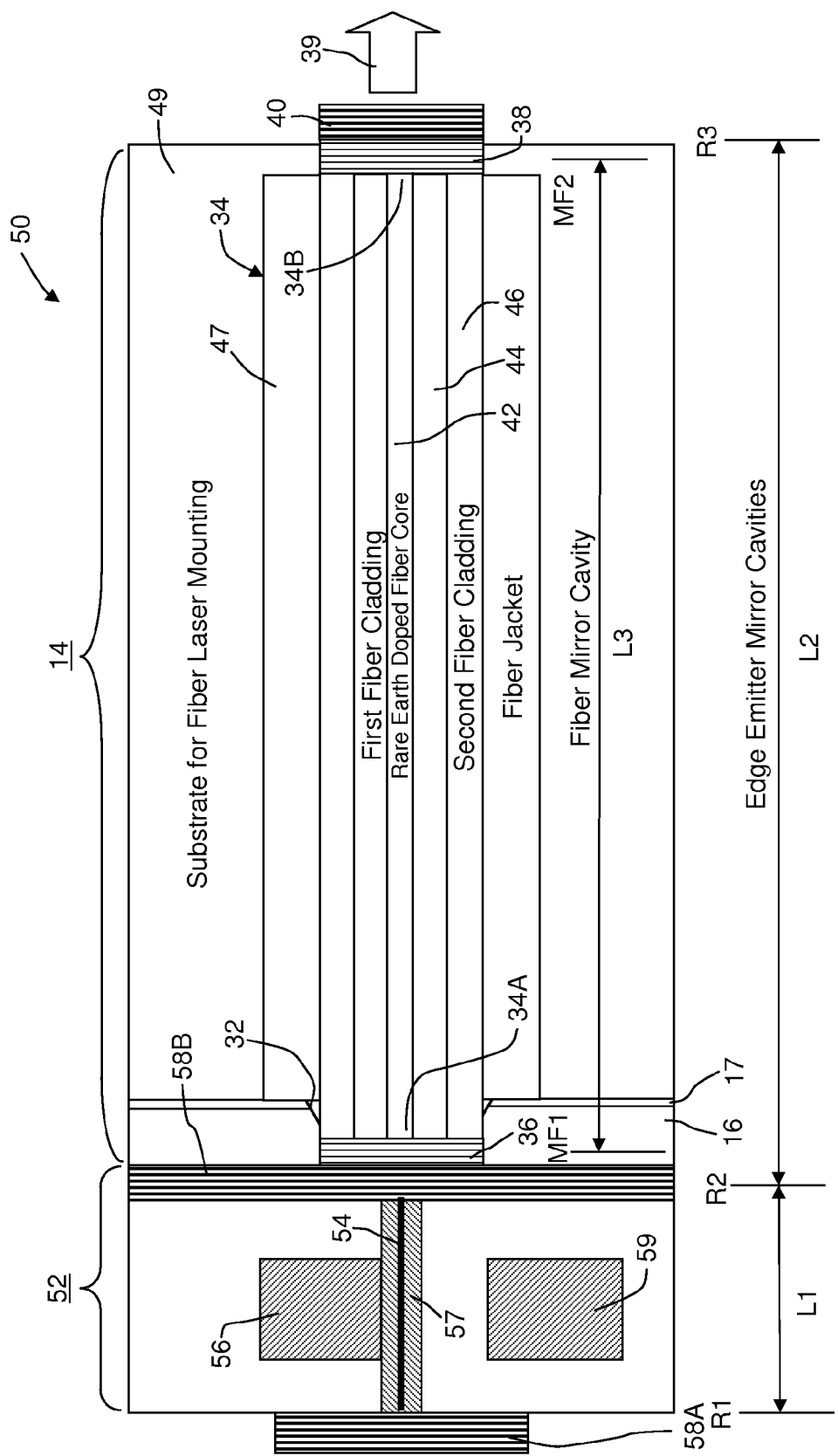
FIG. 2 is a cross-sectional side elevation view of a side emitter pumped micro fiber laser adapted for deployment in this invention.
Figure 6:
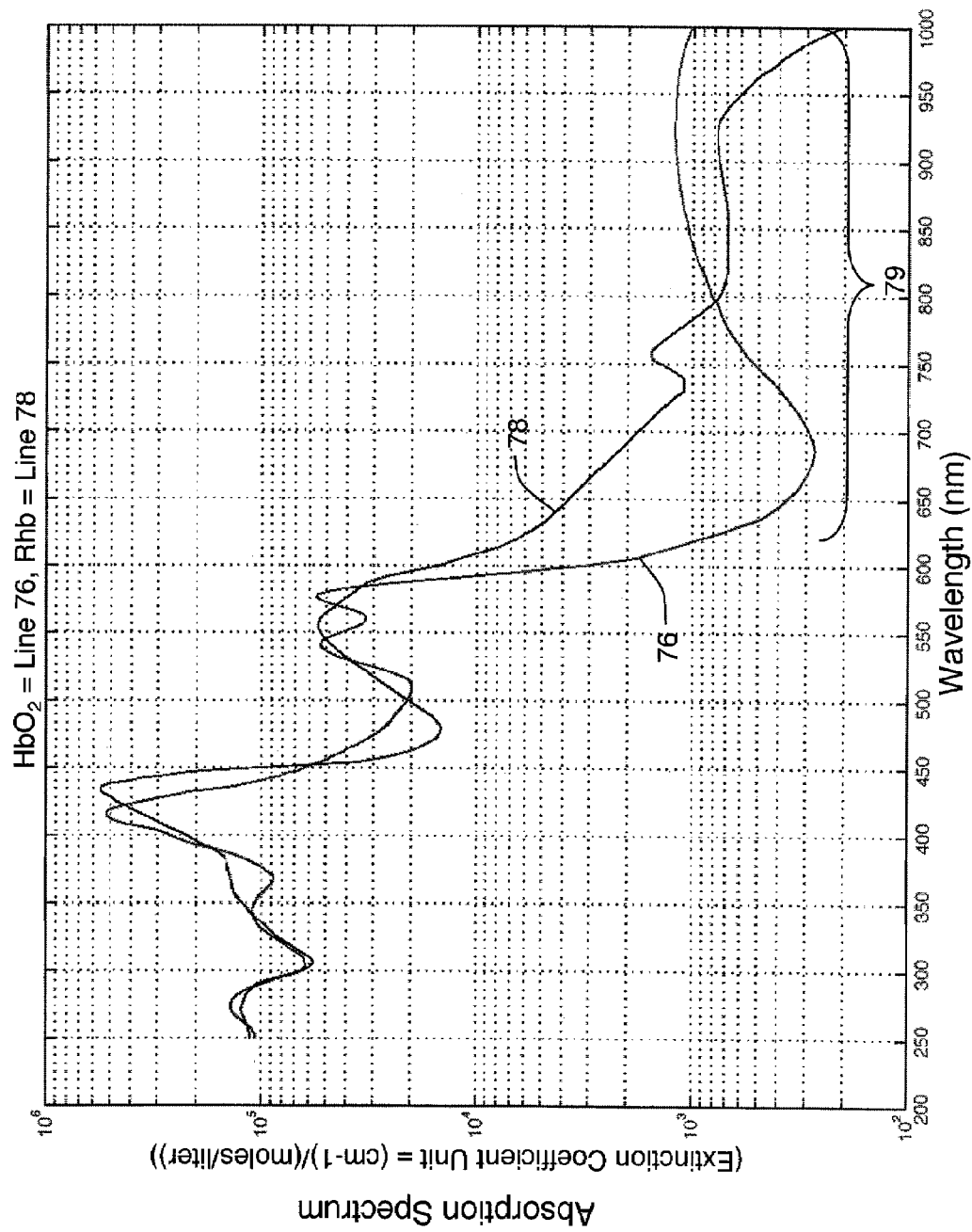
FIG. 6 is a graphical illustration of the absorption spectra over a wide range of wavelengths (200 nm to 1,000 nm) for oxygenated and deoxygenated hemoglobin.

Reference is now made to FIG. 1 which is also similarly disclosed in U.S. application Ser. No. 10/411,637, supra, as FIG. 6. A first embodiment of a semiconductor laser-pumped small-cavity fiber hybrid laser 10 is schematically illustrated in FIG. 1 comprising a surface emitting semiconductor laser 12 and a rare earth doped fiber laser 14. In the illustrated embodiment of FIG. 1, the semiconductor surface emitting laser is also known as a VCSEL, but it will be appreciated by those skilled in the art that an edge emitting semiconductor laser, such as illustrated in FIG. 2, to be discussed next, may also be employed as a semiconductor pumping laser.

Thus, hybrid laser 10 includes VCSEL 12 and a microcavity or small-cavity fiber laser 14. VCSEL 12 comprises substrate 16 on which is formed a vertical optical cavity structure having an optional VCSEL output coupler and cavity mirror 18, gain region 20, and cavity mirror 22, together forming the laser cavity, L1, of pump laser at semiconductor laser 12. Cavity mirror 22 may be a Bragg high reflector and VCSEL output coupler 18 may be a Bragg partial reflector, with reflector semiconductor layers of either cavity mirror epitaxially grown over the substrate 16 as well known in the art. Gain region 20 may comprise an epitaxially grown semiconductor gain layer, and may be, for example, a single bulk active layer or quantum well/barrier region as known in the art. The types of semiconductor materials used in the gain region are typically selected so that the VCSEL 12 oscillates at a desired wavelength. This wavelength is then employed for pumping the fiber laser 14. The types of materials used in the reflectors 18 and 22 are typically selected to provide desired amounts of reflectivity at the desired wavelength, with little or no optical absorption. Reflector 22 is typically made from a semiconductor material, such as AlGaAs, that has high thermal conductivity so as to efficiently conduct heat away from active region 20 to heatsink 28. An electrode 24 may be formed over the Bragg high reflector 22 for passing electrical current through the gain region 20 to a corresponding electrode on the other side of active region as seen at 17. An insulating current barrier 26 may be provided for lateral confinement of the current passing through the gain region 20. Heatsink 28 may be in thermal contact with the epitaxial top of vertical cavity pump laser 12 to provide for efficient heat dissipation. Substrate 16, which may be GaAs or InP, is provided with an aperture 32 to provide an optical output port from VCSEL 12 which output is optically coupled into rare earth doped fiber 14. A first end 34A of fiber 34 receives the coupled radiation from gain region 20 and the optical cavity of laser 12. Fiber 34 may be attached to substrate 16 forming a butt coupling with optional mirror or reflector 18, or may be inserted, at least part way, into aperture 32 and held in coupled position by means of an optical gel which has a refractive index that renders it transparent to pump radiation emitted from laser 12. Both fiber laser 14 and VCSEL 12 may be supported on a substrate or bench 49. A first fiber reflector 36 is disposed at first end 34A of fiber 34 and a second fiber reflector 38 is disposed at a second end 34B of fiber 34. Fiber reflectors 36 and 38 form a fiber laser cavity for fiber 34. Typically, first fiber reflector 36 is a high reflector at the emission wavelength of small-cavity fiber laser 14. First fiber reflector 36 may have a low reflectivity at the pump emission wavelength so that a large fraction of the pump radiation from VCSEL 12 passes through first fiber reflector 36 into fiber 34. First fiber reflector 36 may be a multiple layer dielectric mirror deposited on end 34A of fiber 34, or may be a reflector structure separate from fiber 34. In one embodiment (not shown) for reflector 36 to be separate from fiber 34, first fiber reflector 36 is epitaxially grown as a Bragg reflector on substrate 16, between gain region 20 and fiber 34. In either case, as mentioned previously, first fiber reflector 36 is generally transparent to the pump laser emission wavelength but is highly reflective, i.e., close to 100%, of the fiber laser emission wavelength provided as part of the hybrid laser output at 39. Second fiber reflector 38 at fiber end 34B typically has a reflectivity less than 100% and operates as the output coupler for fiber laser 14. The value of the reflectivity of second fiber reflector 38 may be selected for optimum output coupling, based on a number of system parameters such as the fiber length, pump power, doping level, core diameter, and the like. Also, which is particularly novel in laser 10, is a pump radiation reflector 40 that may be disposed at second end 34B of fiber 34 for reflecting pump radiation that has passed through and into the optical cavity L3 of fiber 34 and its associated cavity reflectors 36 and 38 are not generally absorbing of this pump radiation. This may lead to increased pump absorption efficiency which permits the use of even shorter fibers for fiber laser 14. Furthermore, the device may be configured such that the fiber cavity coupling to the VCSEL laser cavity is high, and pump radiation reflector 40 represents of significant reflectivity contribution to the semiconductor pump laser cavity. Under this circumstance, one is able to achieve resonantly enhanced absorption of the pump laser radiation in the fiber cavity.

In the optimum case, the pump radiation absorption in the fiber cavity can be configured to be the predominant source of photon loss out of the pump laser cavity so that substantially all of the radiation generated in the semiconductor pump laser cavity is delivered to fiber laser 34. In this case, highly efficient pumping of fiber laser 14 can be realized which, in turn, permits significant reduction in the fiber length down into the mm range resulting in an optical fiber cavity that is of very small or micro size in terms of present day utilized fiber lasers. Pump radiation reflector 40 and second fiber reflector 38 may each be multiple layer dielectric mirrors deposited on second end 34B of fiber 34, or may be separate formed from fiber 34.

Fiber 34 has a core 42 which is doped with the excitable species, for example, rare earth doping species such as thulium, erbium, holmium, ytterbium, neodymium, promethium, terbium, praseodymium, or the like. As a specific example, fiber 34 may have an outside diameter of approximately 150 μm and a core diameter of about 6 μm. One or more of these dopants are incorporated into core 42 of fiber 34 and are excited by the pumping radiation from VCSEL 12 which is at the proper pumping wavelength to carry out such excitation. Emitted radiation at output 39 of laser 10 is at a wavelength determined by the specific rare earth specie or species incorporated into core 42 and the reflective properties of fiber cavity mirrors 36 and 38. For example, if the rare earth dopant chosen for core 42 is thulium, the output 39 of fiber laser 14 may yield emission wavelengths in the 2,300 nm range of wavelengths with suitably designed mirrors. In this connection, see FIG. 14 which shows the possible emission wavelengths for a thulium doped fiber laser 14. As further indicated in FIG. 1, Fiber 34 may comprise a double-clad fiber comprising a first cladding 44 surrounding the rare earth species doped core 42 and a second cladding 46 surrounding first cladding 44. Second cladding 46 is then covered with a protective jacket 47. Fiber laser radiation is confined to doped core 42 because the effective refractive index for the fiber laser radiation is less in first cladding 44 than the effective refractive index for doped core 42. Pump radiation from VCSEL 12 is coupled into, and is confined by, first cladding 44, since the effective refractive index for pump radiation in first cladding 44 is higher than the effective refractive index in second cladding 46. The pump radiation, therefore, passes along, through and crisscrossing fiber core 42 and first cladding 44. Optical confinement of the pump radiation from pump laser 12 is typically multimode confinement. One advantage to employing a double-clad fiber in an embodiment for laser 14 is that the coupling efficiency of pump radiation propagating from VCSEL 12 into fiber 34 of fiber laser 14 is very high.

Thus, it can be seen that hybrid laser 10 of FIG. 1 provides for laser emission at two, rather than one wavelength. The VCSEL pump source 12 will, at some level, inevitably provide radiation emission at the output end of fiber laser 14 where pump wavelength reflector 40 is below being 100% reflective. Thus, this pump wavelength emission therefore is of an intensity determined by the reflectivity of the VCSEL mirror, M3, at 40. Thus, by controlling the transmissivity magnitude of mirror, M3, the amount of VCSEL pump radiation can be controlled that is allowed to leak through mirror 40 as part of the laser output 39. This background pump radiation may be put to use as another wavelength for monitoring a spectral characteristic feature, for example, such as an absorption feature, which may be a peak analyte absorption intensity that is at the VCSEL emission wavelength, together with the fiber emission wavelength, thus creating a two wavelength integrated emission source 10.

It will be appreciated, of course, that fiber 34 need not be double clad fiber, and that the pump radiation from VCSEL 12 may be coupled directly into fiber core 44. In such a case, the pump radiation intensity in the core is higher than that with a double clad fiber, but the overall efficiency for coupling pump radiation into fiber 34 may be reduced.

It will be further appreciated that fiber 34 may be a multimode gradient index fiber with an imbedded smaller diameter doped core with single mode or near single mode propagation. This configuration enables the combination of the previously mentioned coupling and propagation benefits of the graded index fiber with the wavelength conversion properties of the excitable species doping. In some embodiments, the length of fiber 34 may be around 1 cm. For such a length, it may be desirable to have a relatively high level of doping of excitable species in fiber core 42. It may also be desirable to have a relatively large core diameter. Also, the refractive index profile of fiber 34 need not be parabolic, and may have some other type of profile, such as a combination of parabolic and refractive index stepped profile or purely refractive index stepped profile. More is said about this matter in U.S. patent application Ser. No. 10/411,637, incorporated herein.

In many configurations, the VCSEL lasing cavity is formed between Bragg high reflector 22 and VCSEL output coupler 18. Pump radiation emitted by this cavity passes into the fiber cavity formed between the fiber reflectors 36 and 38. The pump radiation is absorbed in doped fiber 34 so as to excite the excitable species in fiber 34. Pump radiation reflector 40 at the second end 34B of fiber 44 reflects unabsorbed pump radiation back through the fiber cavity towards VCSEL 12. Thus, in essence, a pump cavity is also formed between VCSEL output coupler or reflector 18 and pump radiation reflector 40. Where the frequency of the pump radiation falls at one of the resonant frequencies of the pump cavity, the pump radiation may be circulated many times within the pump cavity, thus encouraging higher absorption efficiency of the pump radiation within the fiber 34. It is preferred that the excitable species not manifest optical gain at the wavelength of the pump radiation. Where the pump radiation is resonant in the pump cavity, the length of fiber 34 employed for fiber laser 14 may be selected more on optimum gain length, rather than on a minimum length driven by the single pass absorption length of pump radiation in fiber 34, as is the typical approach taken by those skilled in the finer laser design art.

It is also within the scope of this invention to provide a VCSEL 12 that is tunable. To this end, the gain cavity of the VCSEL may be varied to change and tune the wavelength output of the VCSEL by means, for example, of a microelectrically mechanical mechanism as seen in Publication No. WO02/0844826 or U.S. patent application, Pub. No. 2003/0031221A1, respectively, by providing a movable mirror assembly for one of the VCSEL DBR cavity mirrors through an applied voltage or by constructing one of the DBR cavity mirror assemblies to be comprised of a MEMs type of structure. Another approach to vary the cavity length of the VCSEL is by changing the refractive index of one of the DBR cavity mirrors of the gain cavity of the VCSEL as disclosed in U.S. patent application, Pub. No. 2004/0028092. These three patent application publications are incorporated herein by their reference.

Reference is now made to FIG. 2 which illustrates a hybrid laser 50 comprising a semiconductor laser pumped small- or micro-cavity fiber laser which includes small-cavity fiber laser 14 as seen in FIG. 1 but, in the case here, butt coupled to semiconductor side emitter laser 52 which is here shown in this embodiment as a Fabry-Perot laser. Laser 52 may also be a distributed Bragg reflector (DBR) or a distributed feedback (DFB) laser with a feedback grating along and adjacent the laser cavity core. Laser 52 comprises an optical cavity 54 and a pump stripe 57 with a p-contact electrode 56 and a n-contact electrode 59 as known in the art. The back and front cavity mirrors 58 and 60 may be deposited on the laser facets comprising a plurality of dielectric layers that provide the necessary feedback to cause laser 52 to lase at a desired operational wavelength. However, Fabry-Perot laser 52 may have cavity end facets that provide laser cavity feedback to provide lasing with the laser cavity being of a designed length to provide an emission wavelength design capable of pumping micro-cavity fiber laser 14. The description of fiber laser 14 is the same here as discussed in connection with FIG. 1. It should be noted that there will be some compromise in the deployment of edge emitter pump lasers 52 rather than surface emitter lasers 12 in coupling efficiency due to the elliptical emission beam from these types of edge emitter lasers. However, higher output powers are available from edge emitter lasers compared to surface emitter lasers. The edge emitter laser also does not readily lend itself to being fabricated in two dimensional arrays and are much more amenable to linear arrays or bars. Either device, however, can be supported by similar control electronics some of which is depicted in FIGS. 10-13, to be discussed later.

Figure 14:
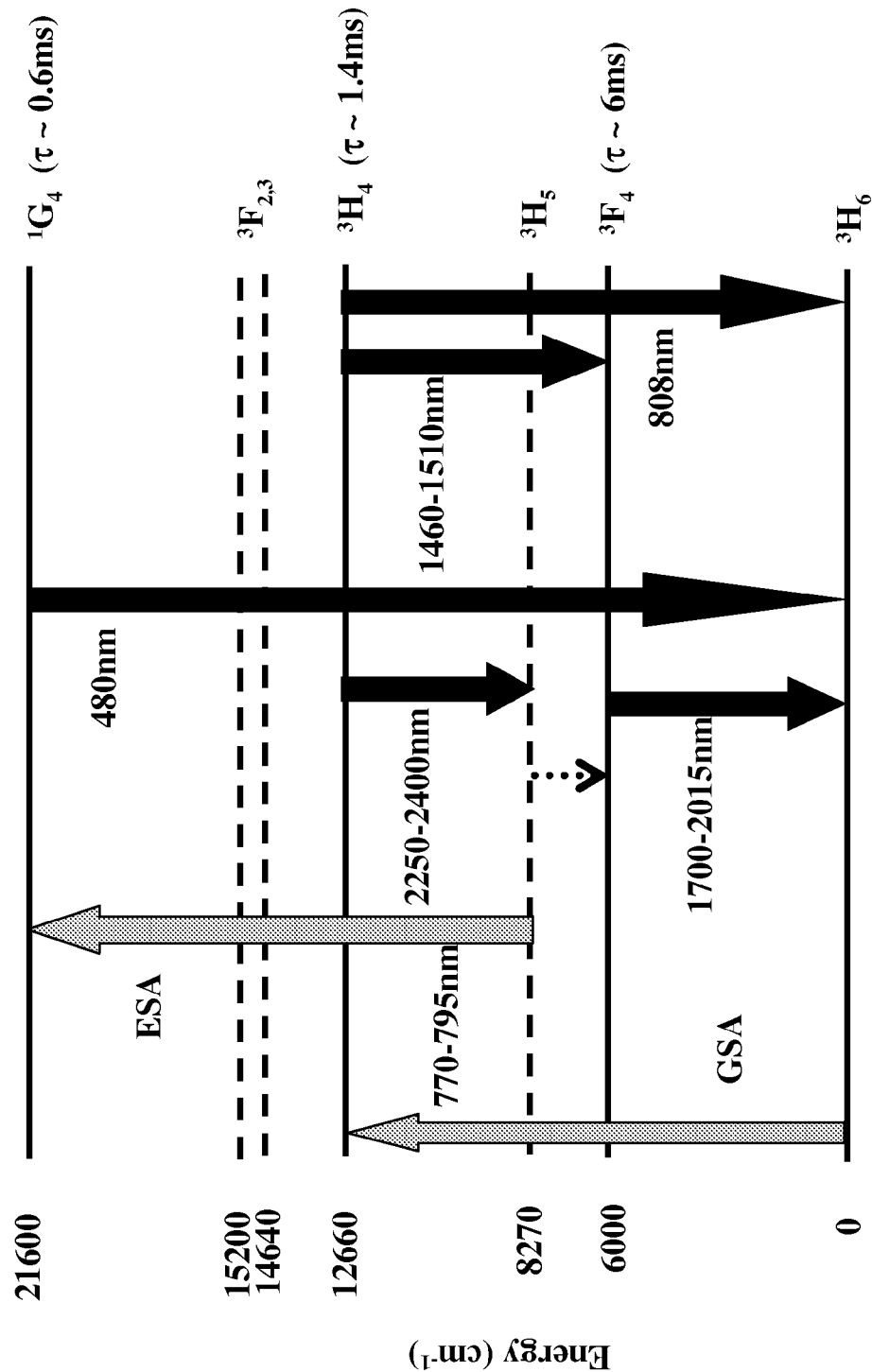
FIG. 14 is an energy-level transition diagram for thulium.

VCSEL pump laser may be used to pump the excitable species into an excited state through the absorption of one or more pump photons. One specific example of a VCSEL pumped laser is a thulium-doped fluorozirconate (ZBLAN) optical fiber. A portion of the transition energy diagram for this system, with a specific absorption/emission pathway highlighted, is shown in FIG. 14. The pump photon absorbed by the thulium ion, $Tm^{3+}$, has a wavelength of around 790 nm. Pumping around 790 nm is well suited to populating transition states leading to laser transitions at 2,300 nm, 1,820 nm and 1,470 nm. Potential for simultaneous lasing at both 1,820 nm and either 2,300 nm or 1,470 nm results from both 2,300 nm and 1,479 nm laser transitions leading to the excited state at $3F_4$ transition for 1,820 nm. As shown in FIG. 14, absorption of this pump photon raises the thulium ion to the $3H_4$ transition level. There are at least two decays paths from this level to the excited state $3F_4$ level. One path, which is accompanied by an emission at 2300 nm, which is a two-step decay via the $3H_5$ level, and the other is a direct transition that is accompanied by the emission of a photon at 1,470 nm. The $3F_4$ level has a transition back to the $3H_6$ ground state level that is accompanied by emission of a photon at 1,820 nm. Laser oscillation may be achieved on both the $3H_4$-$3H_5$ and the $3F_4$-$3H_6$ transitions so that fiber laser 14 may produce radiation at 2,300 nm and/or 1,820 nm. Fiber laser 14 may, thus, be employed to access emission wavelengths substantially longer than the emission wavelengths available currently with VCSEL devices. Such a fiber laser is based on the use of a pump photon, for example, at 780 nm or 790 nm. A VCSEL laser 12 having an AlGaAs active region may be used to generate pump radiation within this wavelength range.

In connection with the transition diagram for thulium of FIG. 14, the transition ranges of wavelengths, such as 1,460 nm to 1,510 nm, 1,700 nm to 2,015 nm and 2,250 nm to 2,400 nm all include wavelengths having high absorption sensitivity for the analyte, glucose, which can be utilized to provide useful information for determining the concentration of glucose in a specimen. Wavelengths in these ranges, particularly those representing wavelength spectral characteristic features, such as represented by positive or negative peaks for glucose absorption, for example, can be generated as emission wavelengths from micro-cavity fiber laser 14 by determining and designing the reflectivity spectra for mirrors or reflectors 36 and 38 applied to fiber laser 14 to create the optical cavity, which can be determined with a significant degree of flexibility employing standard thin film optical coating designs and deposition techniques. Thus, the hybrid laser platform illustrated in FIGS. 1 and 2 enables the realization of a single unitary, compact radiation source with the capability of being able to produce one or more wavelengths over a broad spectral range of wavelengths, some of which are out of the emission wavelength range of semiconductor lasers, employing a fixed pump wavelength from a semiconductor pump laser, such as at a pump wavelength of 785 nm, which pump wavelength may also be one of the emission wavelengths of from hybrid laser 10 or 50.

Figure 3:
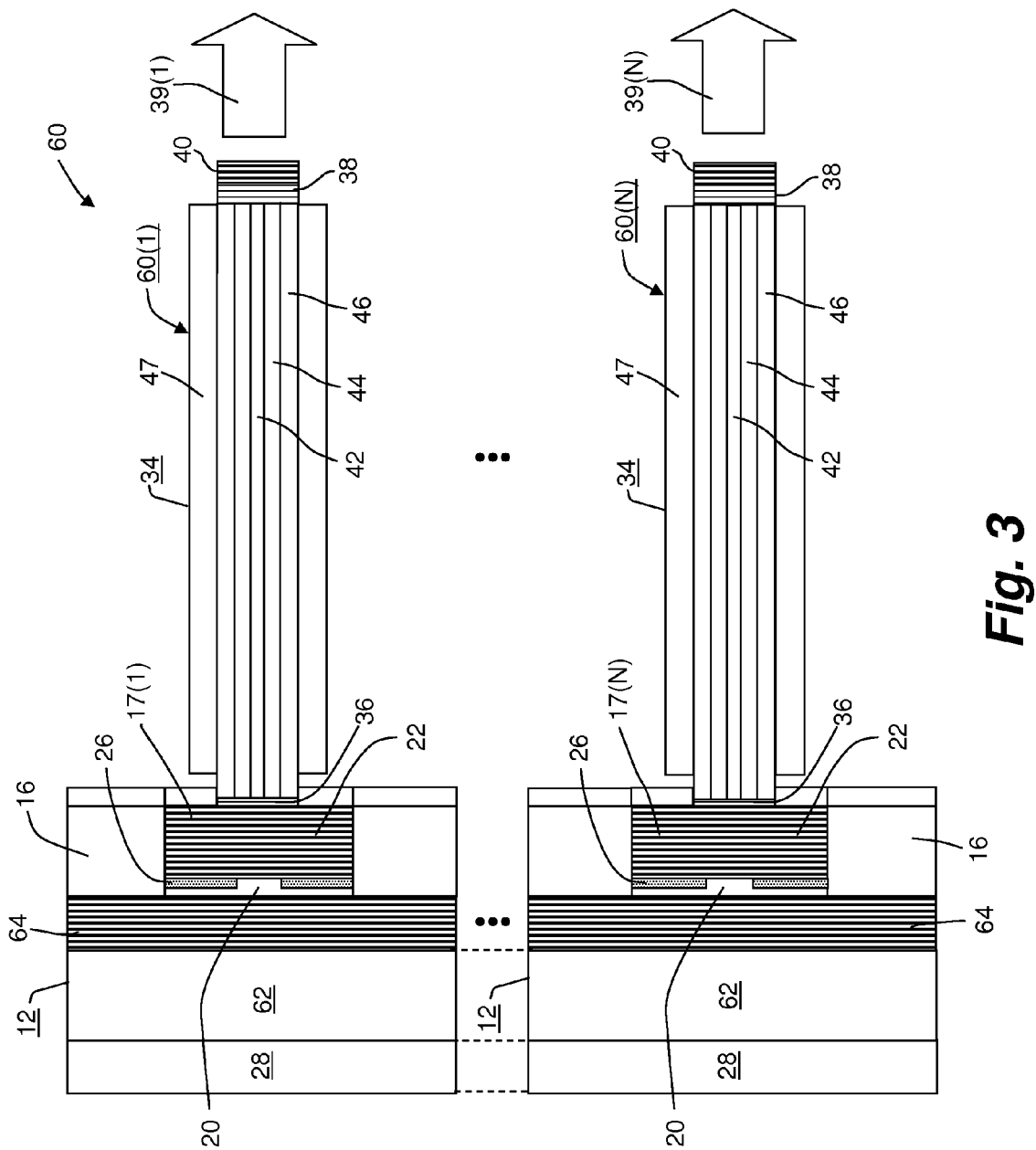
FIG. 3 is similar to FIG. 1 except two or N multiple semiconductor/micro fiber lasers or laser arrays are illustrated, each of which may be operating at a different set of wavelengths.

Reference is now made FIG. 3, and to the semiconductor laser pumped small- or micro-cavity fiber laser array 60 which is another embodiment of the laser that may be utilized in this invention. Laser array 60 comprises a plurality of semiconductor laser pumped micro-cavity fiber lasers 60(1) . . . 60(N) that are formed or epitaxially fabricated on the same substrate. Each laser 60 is substantially identical to laser 10 shown in FIG. 1. However, lasers 60(1) . . . 60(N) may either be all integrated on the same common substrate 16 as shown in previous embodiments, or may have a common substrate 62 as shown in this embodiment, depending upon from which end of the laser array epitaxial growth is initiated on a substrate 16 or 62. Alternatively, lasers 12 in FIG. 3 may be separate or discrete lasers each having their own substrate. In any case, in FIG. 3, lasers 60(1) . . . 60(n) are illustrated as being formed on a single substrate 62 and have a common lower DBR mirror 64. Lasers 60(1) . . . 60(N) may all have the same upper DBR mirror 17 or these mirrors 17 may be constructed as different dielectric mirrors 17(1) . . . 17(N) such that each respective lasers may operate at a different pump emission wavelength. Such an array may also be similar to the arrays illustrated in U.S. Pat. No. 6,693,934, which patent is incorporated herein by its reference, where the integrated VCSEL elements are all fabricated to have different cavity lengths so that each individual VCSEL element emits a different emission wavelength. The embodiment of FIG. 3 has particular utility for many spectroscopy applications where additional wavelengths in the absorption spectrum of an analyte under examination are required in order to extract an accurate measurement of the concentration of analyte in a specimen, for example, at features comprising absorption peaks at a plurality of wavelength positions along a portion of the absorption spectrum of the analyte, which peaks may number, for example, from 6 to 10 or more comprising such absorption wavelength positions of interest. For these applications, multiple VCSEL pump laser/fiber laser units 60(1) . . . 60(N) may be integrated to form a multiple emitter array hybrid device. An example of a preferred embodiment comprises the VCSEL pump wavelength for lasers 12 to be at 785 nm so that the VCSEL pump lasers 12 may all be fabricated on a common substrate 62 and consist of a linear or a two dimensional array, which would be butt coupled or otherwise optically coupled to a linear or two-dimensional array of micro-cavity, doped fiber lasers 12. In another preferred embodiment, the cavity lengths of the VCSEL lasers may be varied across the pump laser array as taught in U.S. Pat. No. 6,693,934 so that each of the VCSEL pump lasers 12 in lasers 60(1) . . . 60(N) can provide different emission wavelengths that are also designed to be at absorption wavelength positions of interest of the analyte, i.e., spectral characteristic features across the characteristic optical spectrum of the analyte that are in the range of possible emission wavelengths provided by VCSEL pump lasers 12. When multiple VCSEL laser/fiber hybrid laser modules are incorporated as a group, modulation frequencies, such as tone frequencies $F_1$, $F_2$ or $F_3$, or more, may be applied separately to each pump laser 12, which is discussed in greater detail later on, and such modulation tone frequencies must be selected so as to avoid any interference between the modulation frequencies of different modules. Since the individual signals can be narrow band while the spectral bandwidth available is relatively large, the proper selection of tone frequencies for multiple modulation of each pump laser 12 can easily be accommodated.

The foregoing laser structures of FIGS. 1-3 are deployed in this invention to basically provide a plurality of different wavelengths for use in analyte concentration determination in a given in vivo or in vitro specimen. Such combination laser structures have not been known that I am aware of in the semiconductor pump laser/fiber laser art. In such a radiation source, the optical emission frequencies of the VCSEL laser 12 and the fiber laser 14 have greatly different electrical modulation frequency dependent characteristics, as is known by those skilled in the art. It is well known that semiconductor lasers can be directly modulated by electrical injection at frequencies well in excess of 1 GHz with little difficulty. This is a result of the relatively short excited state carrier lifetime in a semiconductor laser, which is in the nanosecond range for spontaneous emission and decreases into the sub-nanosecond range for stimulated emission. In contrast, the excited state electronic lifetimes in a fiber laser are longer by several orders of magnitude. This is indicated in FIG. 14 by the excited state lifetime values indicated adjacent to the states corresponding to laser transition excited states in the thulium atom on the right side of that figure. These lifetimes typically range from a fraction of a millisecond to several milliseconds, corresponding to modulation response frequencies of one hundred or several hundreds of Hz range to perhaps into tens of KHz range. Reference to modulation frequencies in these ranges and any intermediate ranges is referred herein as tone frequencies to distinguish those lower frequencies from higher frequency modulations as seen, for example, in the optical telecommunication industry in the GHz range. By simultaneously modulating the VCSEL at two tone frequencies, one greater than 10 KHz and one less than 100 Hz, modulation of its radiation will be imposed on the VCSEL 12 at both of these electrical frequencies, while modulation will be imposed on fiber laser 14 only at the low modulation frequency, as the fiber laser response at the high modulation rate is extremely small and basically nonexistent. Therefore, in the two wavelength emitter system such as illustrated in FIGS. 1 and 2, it is possible with a single suitable broadband detector to measure the signal level at both of these wavelengths, without employing a spectrometer, or employing wavelength dispersive elements to differentiate between different wavelength outputs from the hybrid laser 10, 50 or 60. Thus, by analyzing the strengths of the detector signals at higher and lower tone frequencies, the signal strengths at the two wavelengths can be deduced without the need for a dispersive element, such as a diffraction grating or the like, to optically separate the different wavelengths which is not necessary or required in the context of this invention. Instead, the different frequency signals to the same photodetector can be distinguished in the electrical domain from one another by their different frequency rates as well as their frequency responses to two different types of lasers 12 and 14 having highly different and separate maximum frequency responses.

As a particular example, if fiber 34 has a core containing thulium which is generally doped in the range of 2,000 ppm to 10,000 ppm and VCSEL 12 is designed relative to formation of its respective cavity reflectors or mirrors 18 and 22 for a given cavity length providing an emission wavelength of about 785 nm, fiber laser 14 will be pumped by this emission wavelength providing fiber laser emission wavelengths at 1480 nm, 1900 nm or 2,300 nm. The 2,300 nm wavelength range is of particular interest because it is within a wavelength range that is difficult to reach with any conventional semiconductor lasers. This wavelength range is of particular importance in this disclosure since it contains spectral absorption intensities or other features, such as what is referred to as spectral residuals, which are useful analyte signatures in many important blood analytes, including glucose, while providing at these same feature positions along the absorption spectrum relatively low absorption for water. In this case, cavity reflectors (MF1) 36 and (MF2) 38 may be, respectively, 99.99% and 99% reflecting of 2,300 nm laser radiation in the fiber mirror cavity, L3, but not reflective for fiber laser lasing at 1,900 nm, which is another possible lasing wavelength for thulium as seen from FIG. 14. Also, with a third mirror 40 at the forward end 34A of the fiber cavity, L3, VCSEL 14 operates as a laser in two separate cavities, L1 and L2, where, for example, DBR reflector (R1) 22 may be 99.99% or highly reflective of the 780 nm pump wavelength, DBR reflector (R2) 18 may be 99.10% or partially reflective of the 780 nm wavelength, and output reflector (R3) 40 may be 99.90% or highly reflective of the 780 nm pump wavelength while only 1% or less reflective of the fiber laser 2,300 nm radiation but permitting some of the pump radiation to pass with the laser emission output 39. Thus, output 39 of laser 10 comprises a combination of two separate peak output wavelengths of 780 nm radiation and 2,300 nm radiation.

Another example relative to a thulium doped core double clad fiber laser, is to design reflectors (R1) 22 and (R2) 18 to provide a pumping wavelength at 1,100 nm as can be seen from the energy-level transition diagram for thulium. As can be seen in FIG. 14, there are a set of transition spacing of energy levels for thulium that the thulium atom can absorb multiple 1,140 nm photons. In this case, cavity mirrors 18, 22 and 40 for the pumping wavelength at 1,140 nm are designed to be respectively reflective at 99.90%, 99.10% and 99.99% of this pumping wavelength whereas the fiber cavity reflectors 36 and 38 are designed to be reflective of 480 nm radiation but 1% or less reflective of the pump radiation of 1,140 nm. Thus, in this case, the hybrid laser emission output 39 of laser 10 will be a combination of two separate peak output wavelengths of 480 nm radiation and 1,140 nm radiation. Thus, it can be seen that the semiconductor laser pumped small- or micro-cavity fiber lasers 10, 50 and 60 can provide a plurality of different wavelengths in output 39 that, if designed properly, have utility in many different applications including optical spectroscopy which is the subject of this disclosure, as well as any other application that may require a compact laser generator that provides multiple wavelength outputs and many potentially selective wavelengths in different regions or areas of the infrared spectrum. An example of another application for such a laser utilized in this invention is in LIDAR.

A structural example of the foregoing multi-wavelength application of a semiconductor pump laser/micro cavity fiber laser is illustrated in FIG. 4. In FIG. 4, the semiconductor pump laser/micro cavity fiber laser 10A is the same as laser 10 in FIG. 1 except that, now, the semiconductor pump VCSEL 12 is pumped with two different tone frequencies from tone generators 70 and 72 comprising a lower tone frequency, $F_1$, and a higher tone frequency, $F_2$. These tone frequencies, $F_1$ and $F_2$, are chosen so that $F_1$ is below the maximum frequency response of fiber laser 14 and $F_2$ is above the maximum frequency response of fiber laser 14. In other words, fiber laser 14 will only respond to the modulation frequency below its maximum frequency response, in the case here the lower tone frequency $F_1$, response. In this regard, see again FIG. 14 for the photon lifetime values at different excited states. This phenomenon of doped fibers allows for determination of the laser energy content at two wavelengths by the examination of two different electrical frequency contents: one fiber laser tone frequency appearing at output 39 when modulation is below the maximum frequency response at $F_1$ at an emission wavelength from fiber laser 14 of laser 10A and two pump laser tone frequencies, $F_1$ and $F_2$, appearing at output 39 regardless as to whether or not the tone frequencies are above or below the maximum frequency response of fiber laser 14. The net tone at F1 containing both fiber laser and pump laser contributions, while the net tone at F2 will contain only pump laser contribution. From the amplitudes of these two tones, the independent amplitudes of the energy at the two laser wavelengths associated with the fiber laser and the pump laser can be obtained. Thus, two useful emission wavelengths are achieved by allowing for partial extraction of the pump radiation in conjunction with a single emission wavelength from fiber laser 14, provide two different and distinct modulated energy contents relative to two output wavelengths derived by modulating the semiconductor pump laser 12 at two different frequencies, one above and the other below the maximum frequency response of fiber laser 14.

The following is a specific example of the foregoing relative to a thulium doped fiber laser 14 for laser 10A. The maximum frequency response for fiber laser 14 is approximately around or above 10 KHz. Thus, in order for fiber laser 14 to respond to a modulating tone, the tone must be at a frequency below this tone frequency, such as at a frequency around or below 100 Hz, which easily modulates the fiber laser output. Thus, for example, if frequency driver 70 is operating at $F_1=100$ Hz and frequency driver 72 is operating at $F_2=10$ KHz for a pump laser 12 that is designed to operate at an emission wavelength of about 780 nm, then for a thulium fiber laser 14 that has reflectors 36 and 38 set for any one of the emission wavelengths of 1,480 nm or 1,900 nm or 2,300 nm, the fiber laser emission output will be at one of these designed wavelengths modulated at a frequency, $F_2=100$ Hz, and the pump laser emission output will be at 780 nm modulated at both or two tone frequencies, $F_1=10$ KHz and $F_2=100$ Hz. The emission output 39 is then received by a broadband photodetector 74 with no intervening optical dispersive elements, as previously explained. The resulting detector signal will contain frequency components at $F_1$ and $F_2$, enabling the independent determination of the output power at 780 nm from the amplitude of the signal at F1, and subsequently determining the amplitude of the signal at 1,480 nm, 1,900 nm or 2,300 nm by subtracting the amplitude of the signal at $F_1$ from the amplitude of the signal at $F_2$.

Light sources 10A or 50 modulated in accordance with the discussion of FIG. 4 are well suited for application in two-wavelength spectroscopy, such as for blood oximetry, where the difference in absorption of blood depending on its oxygenation state is employed to deduce the level of oxygen in the blood, and the measurement is typically performed by comparing the absorption at a pair of wavelengths. In this connection, reference is made to FIG. 6 where absorption spectrum of blood where oxygenated hemoglobin is shown at curve 76 and deoxygenated hemoglobin is shown at curve 78. It can be seen from FIG. 6 that there are significant variations in the absorption of hemoglobin according to its oxygenation state in the wavelength range from about 600 nm to 1,000 nm as indicated at range 79. In this range 79, there are significant contrasts between oxygenated hemoglobin at curve 76 and deoxygenated hemoglobin at curve 78. The difference in the spectra at points along these curves can be employed to measure the blood oxygen content. For a blood oximetry application, an erbium doped fiber for fiber laser 14 in either laser 10A or 50 is particularly well suited, as it can also be pumped at 785 nm as well as made to emit at 980 nm or 650 nm. See the transition diagram for erbium in FIG. 15 where these wavelengths are approximately depicted in the transitions from excited states $I_{11/2}$ and $IF_{9/2}$, respectively. Either of these pairs of transitions (785/985 nm or 785/650 nm) may be employed in conjunction with techniques known in the blood oximetry art to extract blood oxygen concentration from relative absorption measurements. An alternative laser 10A or 50 for this application, which may be simpler, is to measure the oxygen blood content by measuring the relative absorption at 800 nm and 1,065 nm, wherein these two radiation wavelengths are acquired by employing a Nd doped fiber for fiber laser 14 with its mirrors 36 and 38 set for emission wavelength at 1,065 nm. Such a compact oximetry device could be clipped to one's finger, such as during surgery, to measure simultaneously the blood oxygen content of the patient as well as the patient's pulse.

Currently, blood oximetry is performed using a pair of light emitting diodes, typically in a pulsed manner, and typically by analyzing the component of the detected signal that is further modulated by the heart rate of the patient being monitored, such as, for example, during surgery. As an example, these LEDs may have major wavelength emission in the range 79 shown in FIG. 6, such as, for example, at wavelengths 650 nm and 980 nm, based upon spectral variation as seen in range 79 of FIG. 6 relative to curves 76 and 78 at these wavelength vicinities. This method results in a level of imprecision due to a variety of optical and biological interferences. However, the above exemplified dual wavelength sources 10A or 50 utilize more precise specified wavelengths, more elaborate modulation techniques, higher overall radiation levels, and, optionally, more than two wavelengths, to provide greater precision in measurement determination with better SNR as well as better immunity to noise and skin pigmentation variations.

Figure 7:
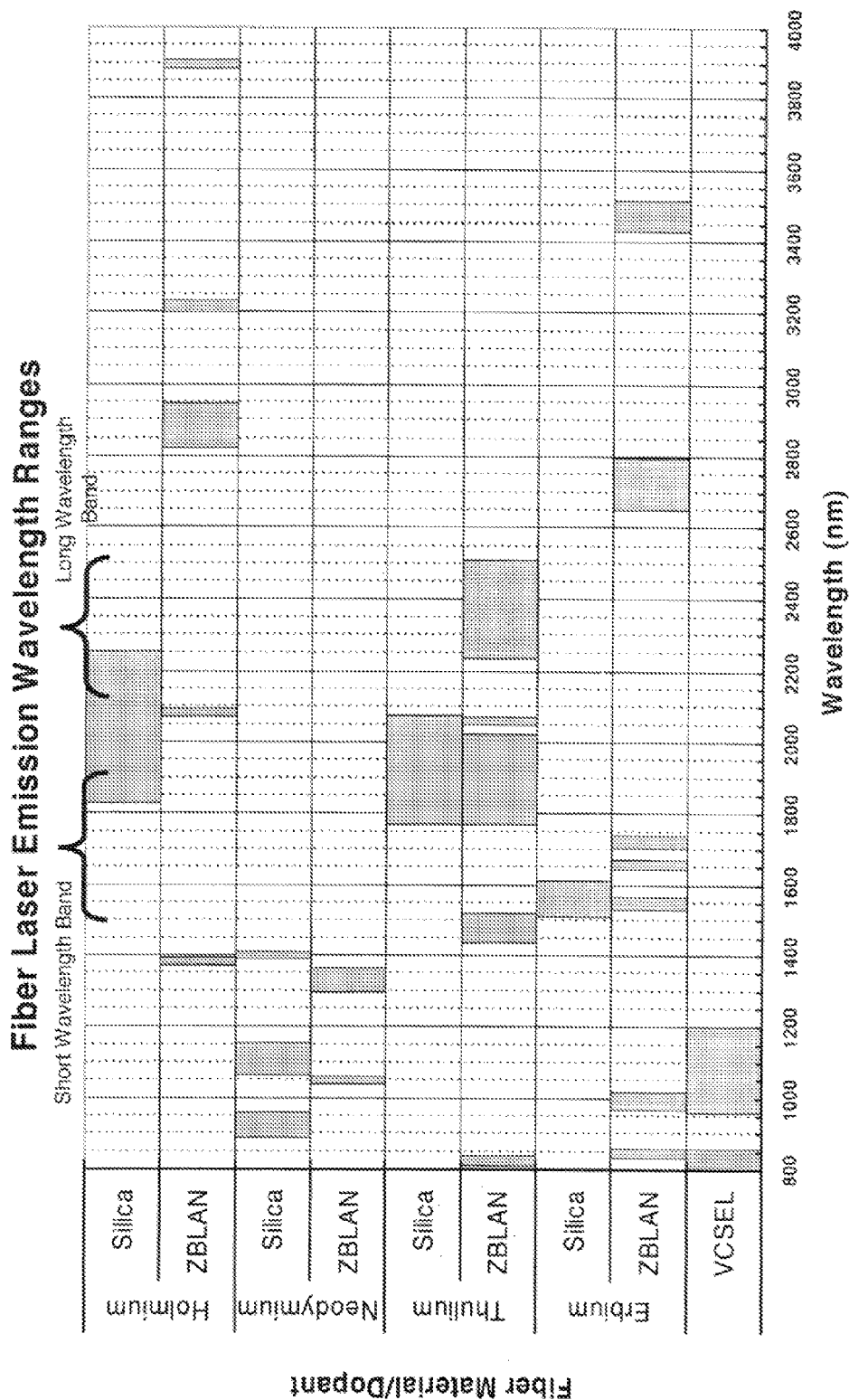
"FIG. 7 is a graphic illustration of several different types of fiber materials and their rare earth dopants showing their fiber laser emission wavelength spectral ranges when pumped near 800 nm."
Figure 15:
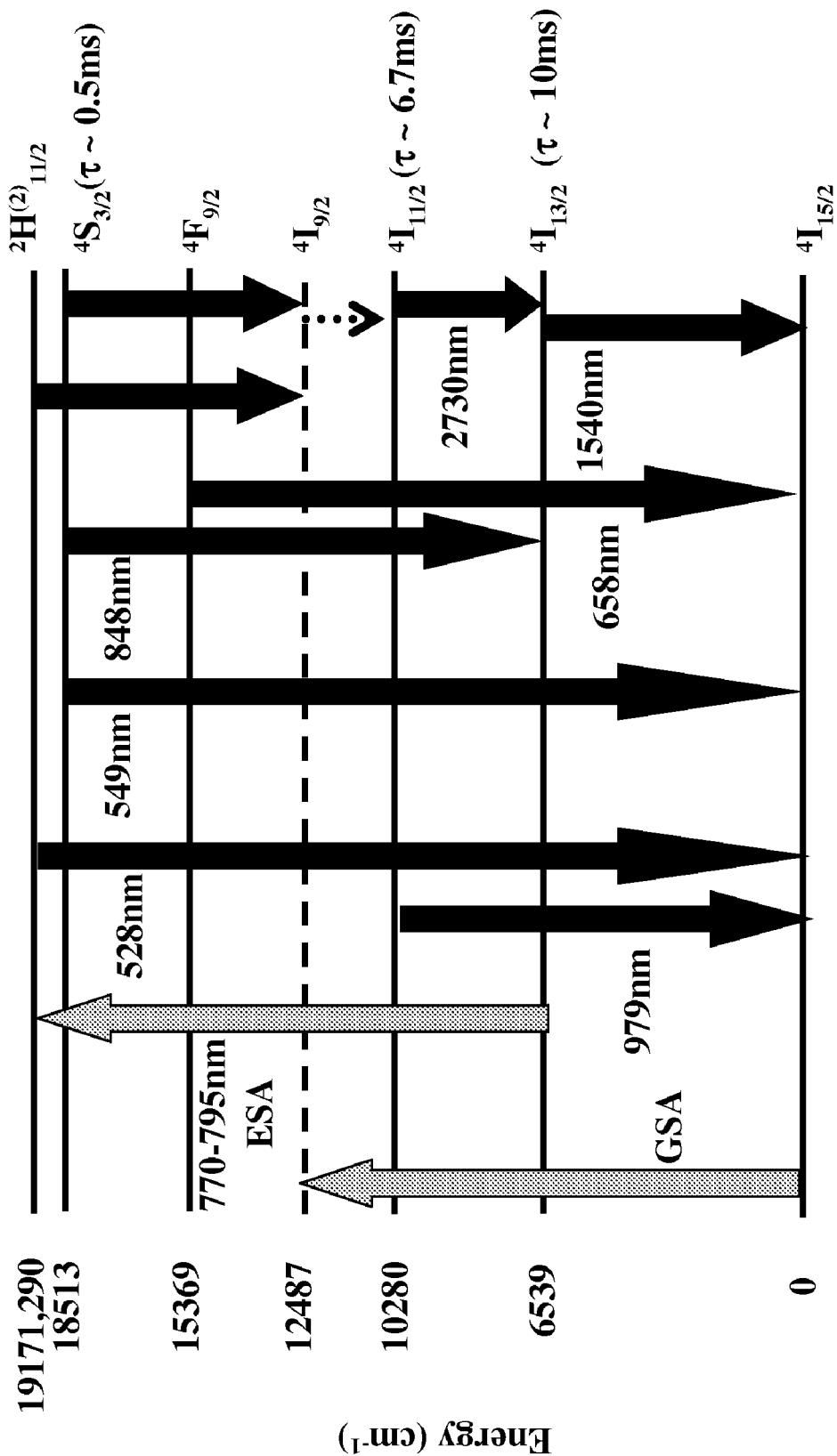
FIG. 15 is an energy-level transition diagram for erbium.

With respect to the forgoing discussions relating to thulium transition states as shown in FIG. 14 and erbium transition states as shown in FIG. 15, spectral monitoring at wavelengths outside of those available with the employment of the emission bands of Thulium doped fibers may be supplemented with rare earth emission bands of other rare earth species such as erbium. It should be noted that an erbium doped fiber has an absorption band which overlaps well with the absorption band of a thulium doped fiber in the 785 nm range, and the overlap is sufficient to provide for the pumping of both Er and Tm doped fibers by semiconductor lasers fabricated on a common substrate. This potentially leads to great reduction in the complexity of optical spectroscopy systems which incorporate mixtures, for example, of Tm and Er for doped fiber cores in fiber lasers 14. The benefit to the additional availability of Er is indicated in FIG. 7, where it can be seen that the emission wavelengths available to Er are complementary to those of Tm in both regions identified as the short wavelength band and the long wavelength band, which are also identified as such in FIG. 8. Note that the emission wavelengths available cover wavelength ranges longer and shorter than the thulium wavelengths, as well as an emission band that covers one of the gaps in the thulium emission range. Thus, Er doped fibers can provide additional capability and functionality in the laser spectroscopy technique of this invention. This advantage can be extended by allowing for simultaneous doping of a single fiber co-doped both with Er and Tm, in which case cross-relaxation processes can be utilized to preferentially populate specific transition energy levels to provide for enhance emission at one desired wavelength relative to another undesired wavelength.

While in FIG. 4, semiconductor small-cavity fiber laser 10A provides for two outputs based upon two different tone frequency modulations, there are numerous examples of applications where more than two-wavelength spectroscopy may be required. For some of these applications, three-wavelength spectroscopy may be sufficient. Further, for many optical spectroscopies where more than three wavelength emissions are required, it is of substantial benefit, for the sake of compactness and simplicity, to extract as many useful, multiple tone modulated, multi-emission wavelengths from a given single multiwavelength laser cavity as is physically possible. FIG. 5 illustrates a semiconductor small-cavity fiber laser 10B which provides for three wavelengths in output 39 where pump laser 12 is modulated with three tone frequencies. Three useful emission wavelengths can be achieved by allowing for partial extraction of the pump wavelength radiation at about 780 nm, for example, in conjunction with two wavelength emission linewidths from fiber laser 14. VCSEL 12 is modulated at three different electrical frequencies, $F_1$, $F_2$ and $F_3$ via tone generators 80, 82 and 84, a first above and a second below the maximum frequency response of fiber laser 14 and a third frequency is an intermediate frequency at which one fiber laser transition responds but not another. This allows extraction of the energy content at the two different fiber laser emission wavelengths plus the pump wavelength by analysis of the three different modulated frequencies present in output 39 and are all detected by broadband photodetector 74 without the requirement of any intervening optical dispersive elements, as previously discussed. Mirrors 36 and 38 establishing the fiber cavity for fiber laser 14 will emit simultaneously at two emission wavelengths. In this connection, observe in FIG. 14 that when hybrid laser 10B is pumped at 780 nm via VCSEL 12, there are two parallel emission routes which both lead to the excited state of the 1,900 nm transition. These two parallel paths are the 2,300 nm transition and the 1,480 nm transition. Since both transitions lead to the excited state of the 1900 nm transition, it is possible, with appropriate design of mirrors, to arrange for simultaneous emission of fiber laser 14 at both 1,900 nm and either 2,300 nm or 14,80 nm. This pair of emission linewidths, combined with the emission wavelength from VCSEL pump laser 12, provides for a three-wavelength laser radiation source 10B. This three-wavelength source may also be used for optical spectroscopy without an additional spectrometer, by appropriate multiple modulation of VCSEL pump source 12. As indicated in FIG. 14, the lifetime of the 2,300 nm/1,480 nm upper level state is 1.4 ms, while the upper level of the 1,900 nm transition has a lifetime of 6 ms. Thus, the modulation rate of the 1,900 nm emission is significantly lower than that of the 2,300 nm or 1,480 nm transition. As a result, it can be seen that by selecting three different modulation tone frequency rates for VCSEL pump laser 12, there are three frequency signals, one to which only VCSEL 12 responds, one to which VCSEL 12 and fiber laser 14 responds at the 2,300 nm/1,480 nm transitions, and one to which all three transitions respond relative to both lasers. From the relative strengths of these three different modulated radiation output signals at output 39, the output power levels at each of the three wavelengths can be readily determined. Additional information on the relative intensities of the wavelengths can be derived from the phase of the modulation, since as the modulation rate approaches and exceeds the cavity electronic lifetime for a given transition, the phase of the response begins to lag the phase of the electrical modulation, resulting in a phase shift in the detected signal which can also be translated into the intensity of the emission signal at a given wavelength.

A specific example of the three wavelength laser 10B is as follows. Pump laser 12 has an emission wavelength of $\lambda_1$ of 780 nm. Fiber laser 14 has its mirrors 36 and 38 designed to provide emission wavelengths $\lambda_2$ and $\lambda_3$, 1900 nm and 2300 nm (or, alternatively, 1480 nm). Three modulation tone frequencies are applied via frequency generators, generator 80 at $F_1$, generator 82 $F_2$ and generator 84 at $F_3$ where $F_1$ is, for example, greater than 10 KHz, $F_2$ is, for example, around 1 KHz and $F_3$ is, for example, around 100 Hz. As a result, hybrid laser output 39 will contain the three signal wavelengths at $\lambda_1$, $\lambda_2$ and $\lambda_3$ where $\lambda_1$ will be modulated at $F_1$, $F_2$ and $F_3$, $\lambda_2$ will be modulated at $F_2$ and $F_3$, and $\lambda_3$ will be modulated at $F_3$. Photodetector 74 will detect $F_1$ which is proportional to the optical power at $\lambda_1$, $F_2$ which is proportional to the optical power at $\lambda_1$ and $\lambda_2$, and $F_3$ which is proportional to the optical power at $\lambda_1$, $\lambda_2$ and $\lambda_3$. The detected amplitude at these frequencies, when transmitted, reflected, or scattered from a sample being measured, is an indication or measurement of the spectral absorption of an analyte under examination that has known peak features of peak intensities, for example, at $\lambda_1$, $\lambda_2$ and $\lambda_3$, such as absorption positive peak intensities or negative peak intensities across a portion of the characteristic optical spectrum, such as the absorption spectrum or spectral residuals of the analyte.

Therefore, a primary feature of this invention is a hybrid surface emitter or side emitter pump laser/fiber laser unit 10A or 10B or 50 which simultaneously emits at a plurality of wavelengths, and for which the amplitudes of oscillation at the plural wavelengths can be independently determined by modulation of the pump laser 12 or 52 at an appropriate set of frequencies, without the requirement of an optical wavelength dispersive element, and with detection of the multiple amplitudes at the multiple frequencies determined by employing a single photodetector and a frequency analyzing circuit.

As previously indicated to some extent before, fiber laser 14 can be doped with different kinds of rare earth species. In graphic diagram of FIG. 7, there is shown a summary of the emission wavelength ranges accessible to a key set of rare earth ions, including holmium, neodymium, thulium or erbium. The fiber emission wavelength ranges are illustrated with examples of different rare earth species as doped in either silica fibers or ZBLAN fibers, which fibers are known in the art. Shown are the potential wavelength ranges for either fiber type that may be employed as fiber lasers 14 with a core doped with holmium, neodymium, thulium or erbium. The wavelength ranges or bands are illustrated in the diagram by the grey-textured rectangles for each such rare earth doped ZBLAN fiber or silica fiber. It can be seen clearly from FIG. 7 that the spectral range of emissions for the different core doped fibers is significantly affected by the host glass material of the fiber which could also include other glass materials such as, for example, fluoride glass fibers.

Also shown in the diagram of FIG. 7 near the bottom is the emission wavelength ranges for VCSEL lasers 12. For VCSEL lasers having pump emission wavelengths near or around 800 nm, a set of emission wavelengths for depicted fiber lasers span a broad bandwidth of the wavelength spectrum including those of interest for the examination of analytes, particularly those in blood. This means that all of these wavelengths within the ranges depicted in FIG. 7 are available to the combination of rare earth dopants and host glass fibers exemplified in this diagram with pumping near 800 nm. As a further example, with the employment of holmium, an energy transfer mechanism exists whereby co-doping with thulium allows for optical pumping of thulium atoms in the 800 nm wavelength band followed by energy transfer to the holmium atoms results in fiber laser emission wavelengths also in the holmium wavelength bands. Thus, all of the wavelength emission transitions shown in FIG. 7 are potentially available via a VCSEL laser pumping at or around 800 nm.

Figure 8:
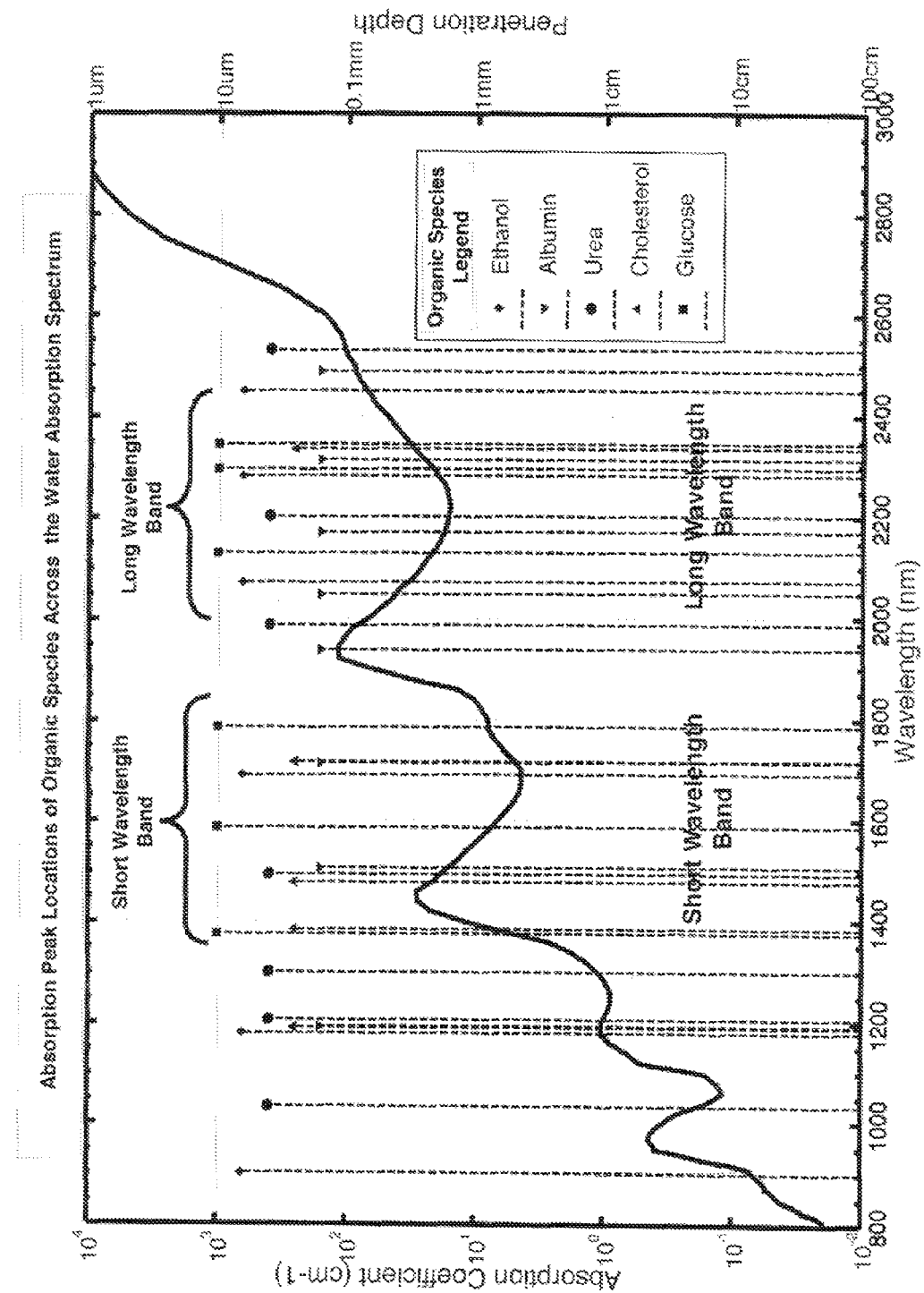
FIG. 8 is graphical illustration of the absorption coefficient curve for water across a wide spectral range (800 nm to 4,000 nm) together with radiation depth penetration, and peak positions of spectral characteristic features comprising the spectral characteristic features of several biologically interesting analytes or species superimposed on the water absorption curve.

Reference is now made to FIG. 8 which graphically illustrates the absorption spectrum of water in the near infrared and peak positions of spectral characteristic features of several biologically interesting species superimposed on the water absorption spectrum. Consideration of the water absorption spectrum is paramount because of the high water content in human biotissue and the strongly wavelength dependent absorption of water which directly effects the optical penetration depth of impinging radiation into the biotissue specimen under examination. As seen in FIG. 8, moving along the full length of the wavelength axis from 800 nm to 3,000 nm, the optical penetration depth in water decreases from nearly 1 meter to less than 1 micron. Also, note that the biotissue spectral characteristic features, such as peak intensities, for the analytes, ethanol, albumin, urea, cholesterol and glucose in blood, have broad absorption spectrums that overlap. Thus, in order to achieve a highly accurate measurement of any one of these analytes in a biotissue specimen, it is necessary to examine a plurality of these features across the absorption spectrum at multiple wavelengths with high sensitivity in order to reliably extract a sufficient sampling containing relevant chemical concentration information from the specimen. The accuracy as to examining wavelengths transmitted to the analyte under examination, such as can be generated from the hybrid lasers 10, 50 or 60, is an important aspect of this invention, particularly where the spectral characteristic features in the near infrared spectra of many of these aforementioned analytes are in close proximity to one another. With hybrid lasers 10, 50 or 60, the predetermined and necessary peak absorption wavelengths can be designed into one or more hybrid lasers of this invention to provide for accurate multi-wavelength spectral probing of any one of the species or analytes relative to the others in same biotissue specimen.

As indicated previously, monitoring of blood glucose levels is a key application of this invention. Glucose has important features in its absorption spectrum in the wavelength range from 800 nm to 3,000 nm, with particular significant features in the range of 2300 nm. These spectral features overlap well with the laser emission capabilities of the thulium doped fiber laser system. The absorption spectrum for other key analytes in the analysis of blood for glucose, some of which are shown in FIG. 8, are also prominent analyte features in blood, along with glucose and water. Greatest sensitivity to glucose will be obtained by measurement at wavelengths where these other absorptions, other than glucose, are lowest. In any case, data analysis is facilitated by acquisition of data at one or more of the spectral characteristic features of glucose such as its absorption peaks as marked in FIG. 8 in the short wavelength band and/or in the long wavelength band. Similarly, data on absorption at the peaks of other potentially interfering species or analytes, such as albumin, may be useful in reducing the number of required spectral characteristic features required for glucose. The several peak features in the glucose spectra are also wavelengths that may be added to the set of potential monitoring wavelengths. Thus, it is generally found that, by monitoring the spectral absorption or scattering at a number of wavelengths in the range, for example, from about 4 to about 16 spectral characteristic features, it is possible to extract, with good resolution, the glucose composition of a sample or specimen.

Figure 9:
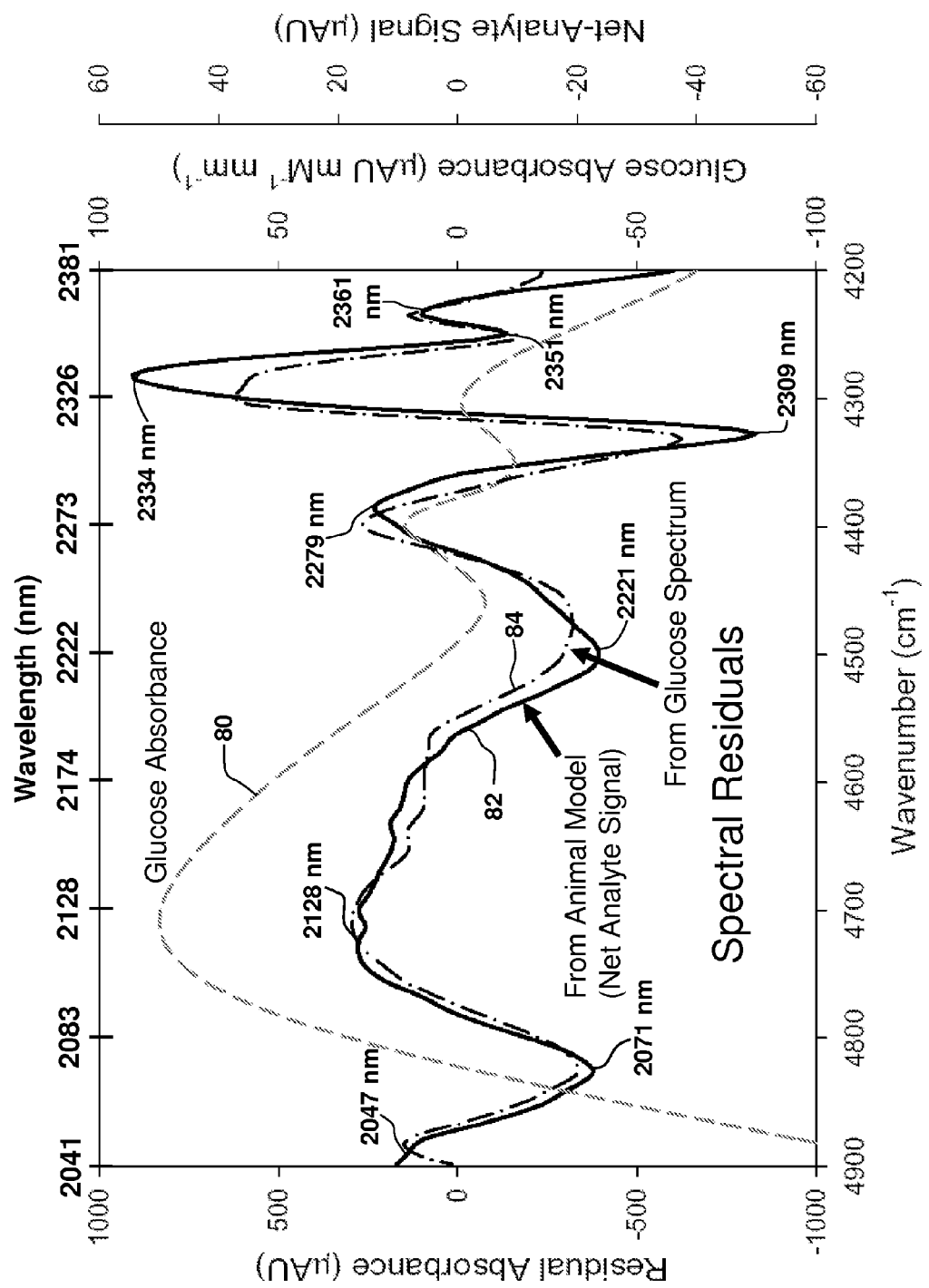
FIG. 9 is a graphical illustration of glucose absorbance and its spectral residuals as determined from two different analytical approaches, partial least squares spectral analysis and net-analyte signal analysis.

With reference to FIG. 9, discussion now turns to further examination of glucose absorption spectrum. Much is known about the optical transmission and scattering properties of glucose as set forth in a myriad of technical papers and patents in the field of glucose testing and analysis. Recent experiments utilizing FTIR spectroscopy within the 2,000 nm to 2,500 nm spectral band has demonstrated important insights into the spectral structure of glucose-containing specimens. Professor Mark Arnold and co-workers at the University of Iowa have performed research into noninvasive in vivo spectroscopy of blood analytes and have achieved important results in the development of statistical/analytical models for quantitative analysis. Some of this work may be directed to the issue of wavelength number and feature position of glucose across a portion of the infrared spectrum as illustrated in the article, J. T. Olesburg et al., "In Vivo Near-Infrared Spectroscopy of Rat Skin Tissue with Varied Blood Glucose Levels", *Proceedings of the SPIE—The International Society for Optical Engineering*, Vol. TBD, pp. TBD, 2004, which article is incorporated herein by its reference. FIG. 9 herein is reproduced from that article and shows glucose absorbance in $\mu AU$ $nM^{-1}$ $mm^{-1}$ at dashed line curve 80 for pure glucose as well as two superimpose analyte signal models comprising the net analyte signal at the solid line curve at 82 and the partial least squares extracted glucose spectrum at the dash/dot curve 84. These two model approaches illustrate what is called "spectral residuals" illustrating a plurality of features comprising here both positive and negative peak intensities across the residual absorbance spectrum. The residual spectrum after removal of baseline factors from the glucose absorbance spectrum is simply the net analyte signal as define in the articles of Lorber entitled, Error Propagation and Figures of Merit for Quantification by Solving Matrix Equations", *Analytical Chemistry*, Vol. 58, pp. 1167-1172, 1986 and of Lorber et al. entitled, "Net Analyte Signal Calculation in Multivariate Calibration", *Analytical Chemistry*, Vol. 69, pp. 1620-1626, 1997, which articles are incorporated herein by their reference. It can be seen from FIG. 9 that curves 82 and 84 they are highly comparable or almost trace one another indicating the accuracy of spectral residuals for glucose in a glucose analyte sample. This provides, therefore, such as seen curve 82, a reliable net analyte signal (NAS) with spectral residual features, separate from or along with the absorption spectrum of pure glucose at curve 80, that can be utilized to determine glucose concentration accurately in the residual absorbance spectrum, particularly over a spectral range of about 2,041 nm to about 2,381 nm. As seen in FIG. 9, there are spectral residual features along the NAS spectrum 82 at 2,047 nm, 2,071 nm, 2,128 nm, 2,221 nm, 2,279 nm, 2,309 nm, 2,334 nm, 2,351 nm, and 2,361 nm. Note that these spectral residuals provide significantly more spectral structure than from pure glucose at 80. These multiple features provide a sufficient spectral span and resolution that will be adequate for sampling the NAS at sufficient density to extract glucose concentrations information. Thus, an optical spectroscopy system of this invention may be restricted to a discrete set of wavelengths within this span in order to determine the blood level of glucose, as demonstrated by the spectral features of glucose at a number of positions as seen from FIG. 9. As seen in conjunction with the fiber emission wavelengths of FIG. 7, many of these spectral features or absorption wavelength positions, if not all, are achievable with the hybrid laser 10, 50 or 60 according to this invention through proper design of the laser cavity mirrors 36 and 38 as previously discussed. Although semiconductor lasers have been demonstrated which can emit radiation in the 2,300 nm range of wavelengths, none yet have proven to be reliable relative to efficiency at modest power levels and reliable over time with spectral stability that is required for this type of optical spectroscopy.

Figure 10:
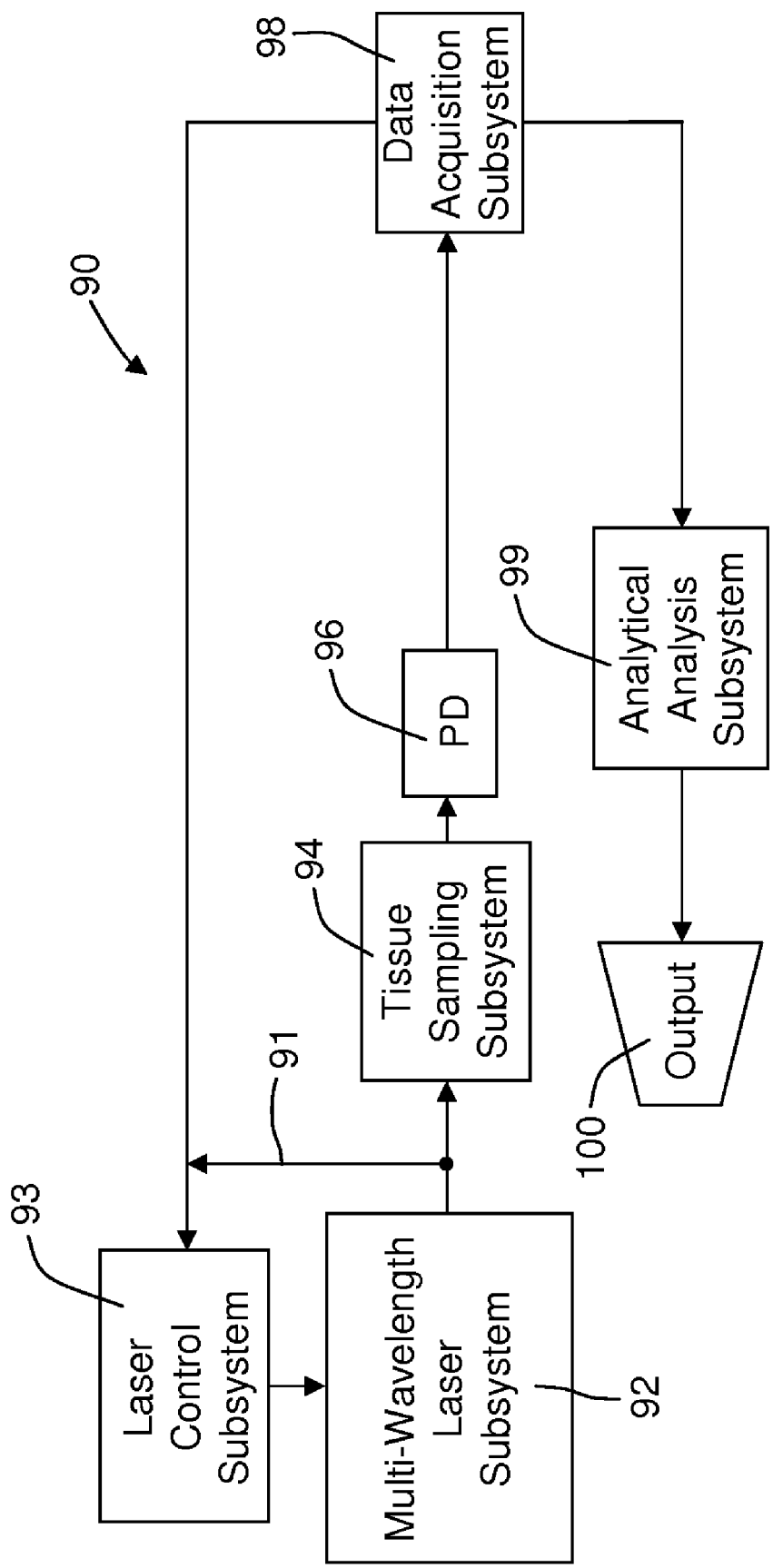
FIG. 10 is a simple schematic diagram of a first multi-wavelength spectrometer system employing this invention.

In the glucose monitoring system of U.S. Pat. No. 6,574,490, supra, there is illustrated in FIG. 1 of that patent a 45 watt tungsten-halogen system having a sophisticated fiber optical system for radiation delivery and collection, a single low noise NIR detector, and a specially designed low noise Fourier transform infrared (FTIR) apparatus in order to achieve clinically meaningful noninvasive blood glucose data. However, since the laser multiwavelength radiation sources of this invention are modulated with multiple tone frequencies relative to different generated wavelength signals, taking advantage of the much slower response time of modulated fiber lasers relative to the much faster response of semiconductor lasers, two important improvements are achieved in system 90, as shown in FIG. 10, over the system as disclosed in this patent. First, the FTIR apparatus of patent '490 can be completely eliminated, and the different optical probe wavelengths generated by one or more hybrid lasers 60 can be readily identified by their modulation tone frequencies at photodetector 96. Second, the effective photodetector bandwidth for each modulated wavelength signal can be greatly reduced by the use of phase sensitive detection techniques resulting in far less laser power in the mW range required to achieve an acceptable SNR. The SNR of system 90 is superior over the system of patent '490 by 1.1 dB where that system requires a radiation source of at least 3.87 W within the spectral range of interest from the 45 W radiation source and a detector bandwidth of 1,000 Hz within the FTIR system in order to obtain the desired spectral resolution.

It is noted that a potential alternative to the halogen lamp of patent '490 as well as the multi-wavelength channel hybrid laser approach of this application is the replacement, in particular of either radiation source with a light emitting diode (LED) or LED array. However, the spectral width of an LED emitting radiation in the 2,300 nm region is about 200 nm with an output power of about 1 mW so that a group of two or three LEDs would cover the combination spectral band covered by the optical spectroscopy systems of the present invention. Although such LEDs can be independently modulated in a manner similar to lasers, their broad spectral width greatly increases the sampled spectral range of each LED channel. Therefore, if the sampled point density required exceeds more than two or three data points or features over the 2,000 nm to 2,300 nm spectral range, it is most likely that LED source modulation will provide inadequate resolution and also an optical dispersive element will be required as well, in order to separate out the different wavelengths for examination. However, once such a dispersive element is inserted in the optical output, which is not required in the present invention, one loses the benefit of a compact system as well as much of the advantage of a phase sensitive detection system because optical output will be greatly reduced. Also, LEDS have roughly three orders of magnitude less spectral power density than a 45 W halogen lamp. Thus, the LED spectral power density will be degraded by the same magnitude of order, that is, three orders of magnitude or about 30 dB. Relative to the FTIR/halogen lamp based system, in contrast, the system of this invention will equal or surpass the SNR of the FTIR/Halogen system. Thus, LED based systems are not a viable alternative to the system of this invention.

Figure 11:
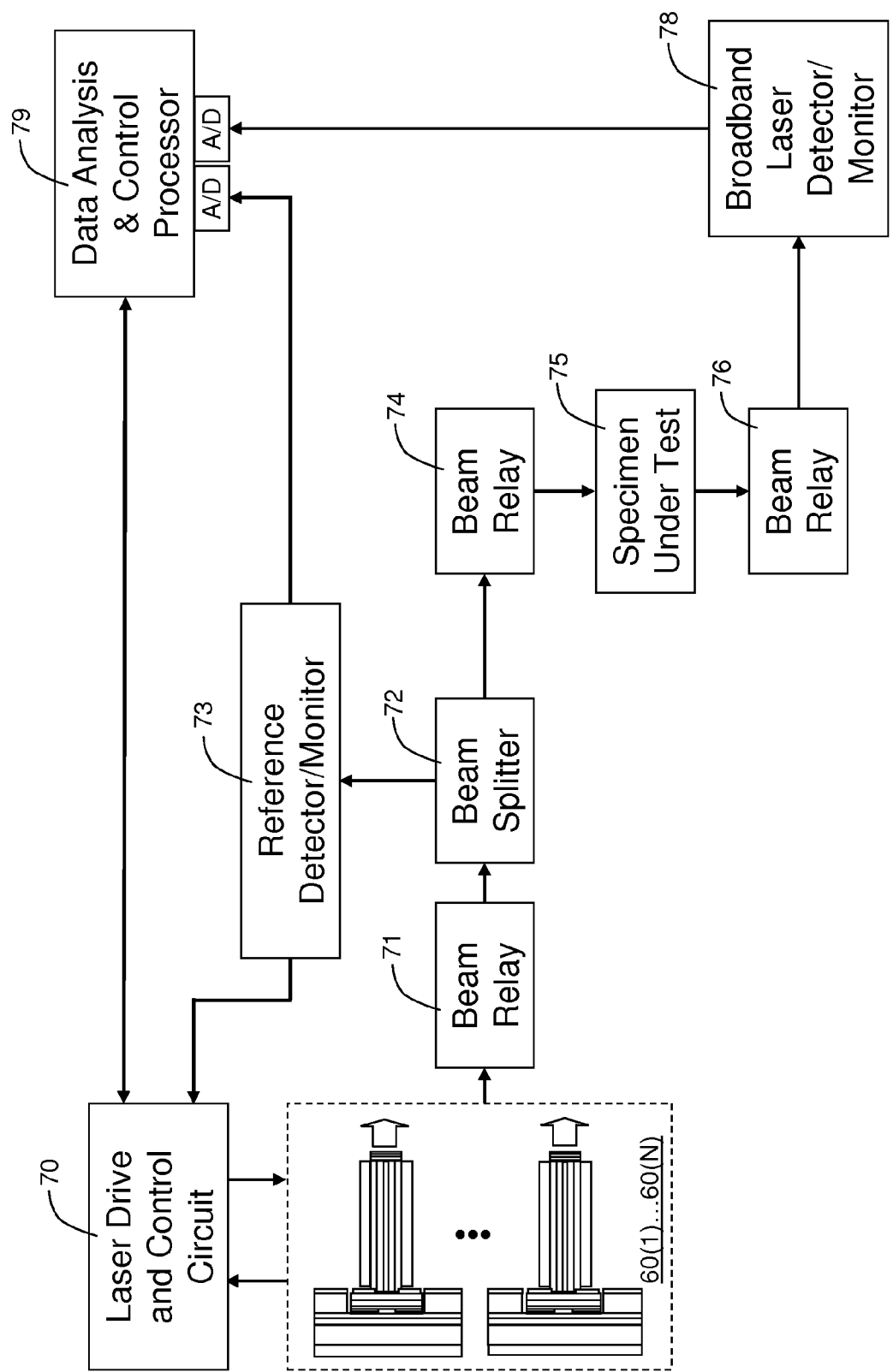
FIG. 11 is a simple schematic diagram of a second multi-wavelength spectrometer system employing this invention.

Reference is now made to FIG. 10 which illustrates in a block circuit diagram a multiwavelength laser spectroscopy system 90 for use in connection with the hybrid lasers 10, 50 or 60, previously discussed. System 90 comprises a multi-wavelength laser subsystem 92 that may be comprised of hybrid laser 10, 10A, 10B, 50 or an array of hybrid lasers 60 as illustrated in FIG. 3 as well as also seen in FIG. 11. Subsystem 92 includes the laser modulated drivers as well as other control electronics, some of which is illustrated in the multiwavelength laser spectroscopy system embodiment of FIG. 12. As an example, subsystem 92 may contain a set of five modulated lasers 60(1) . . . 60(5) with each capable of providing an output power of about 1 mW for a total subsystem of 5 mW of power. Subsystem 93 is the laser control subsystem that controls the operation, including laser current biasing, as well as the multi-frequency modulation of semiconductor pump laser 12 or 52 which also is shown in more detail in FIGS. 12 and 13. The power of these hybrid lasers is directed on a biotissue specimen at tissue analyte sampling subsystem 94 where the output is detected by a broadband photodetector 96. Although the detector itself is broadband to accommodate the total span of the several tones at which the several pump lasers are modulated, the effective photodetector bandwidth for measuring the amplitude of each of the tones may be reduced to very low values, by the utilization of phase sensitive, or "lock-in" detection, as is well known in the art. Photodetector 96 may thus have an effective detection bandwidth of 0.1 Hz or less for each of the individual tones to be detected as a measure of signal power. The modest power levels in the 1 mW range are enabled by these narrow detection bandwidths. An even narrower bandwidth than 0.1 Hz can be achieved for photodetector 96 by employing digital lock-in amplifier techniques. A small portion of the multi-frequency output from subsystem 92 may be provided to laser control system 93 as feedback via line 91 relative to control of signal intensity through bias change on pump lasers 12 or 52 as well as wavelength locking, although the wavelength outputs of these laser need not be lock onto specific wavelengths, but the wavelength feedback may be employed to insure that the emission wavelengths of laser 10 or 50 are within a desired, predetermined bandwidth of operation. Subsystem 94 includes a platform to either hold and position the example or may be a means to properly hold the apparatus in the form of a handheld device in a predetermined relationship relative the in vivo tissues such as human skin. As an example, subsystem 94 may have an engaging mechanism at the front of the device to provide a predetermined gauging of the multi-frequency output relative to the surface of the biotissue specimen under examination such as an arm where photodetector 96 is adjacently disposed to collect scattered and/or reflected radiation for the optically examined tissue. On the other hand, subsystem 94 can be designed to work in a transmissive mode where photodetector 96 is held in opposed relation to the multi-frequency output with the biotissue specimen positioned in the beam path between the output and the photodetector, such as in the case, for example, in the employment of human biotissue in the form of an ear lobe. Data collected by photodetector 96 is provided in the form of photocurrent analog signal supplied to data acquisition subsystem 98 wherein the lock-in amplifier will typically be preceded by a transimpedance amplifier and minimal additional analog processing such as low pass filtering to provide a good analog voltage signal which has a magnitude or amplitude component and a phase component, prior to conversion to digital form via a high precision analog to digital converter with about 24 bits of resolution. Once the signal is digitized, it is processed within a digital signal processor (DSP) which performs the function of multi-tone phase sensitive detection for the several tones simultaneously present on the photodetector sensor. At the DSP, the amplitudes as well as phase differences of the multi-tone frequency signals from the biotissue specimen are determined, which is data representing various wavelength positions or spectral features along the analyte wavelength spectrum or the NAS spectrum, and is compared with known spectral data, stored in memory, having experienced no spectral absorption which may, respectively, be employed to derive specimen modulated signal components and reference modulated signal components. It should be noted that the DSP also may typically provide for generation of the modulation tone frequencies that are provided to the semiconductor lasers 12 at subsystem 92. As between the reference modulated signal components and the specimen modulated signal components, the difference between respective modulation signals will be a DC value which is proportional to the signal amplitude and the difference in amplitude between the reference signals and the specimen received signals which are proportional to the magnitude at a particular absorption wavelength feature of the analyte. This information is passed onto analytical analysis subsystem 99 for matrix and statistical analysis and final determination from the multi-point or spectral residual data indicative of the concentration of the analyte in the biotissue specimen under examination, which is provided as an output 100. Furthermore, data acquisition subsystem 98 also provides information to laser control subsystem 93 as to characteristics of the optical output relative to intensity which can also be correlated to an excessive variation in wavelength output, although small changes in wavelength are not critical since the bandwidth of sensitivity at the spectral features may have a comparatively broad linewidth.

FIG. 11 is a further embodiment of an optical spectroscopy control system illustrated in connect with a plurality of array hybrid lasers 60(1) . . . 60(N) where the multi-frequency/multiple wavelength outputs are provided to a specimen under examination, which is indicated at 75. In this embodiment, by comparison of the electrical modulation spectral amplitudes of the collected signal to those of the incident signal, the spectral absorption characteristics of an analyte, such as glucose, can be deduced. From these absorption characteristics, and with appropriate selection of the set of wavelengths employed, the concentration of a desired analyte can be deduced. Multi-frequency/multiple wavelength outputs from array 60(1)...60(N) are provided to beam splitter 72 via a beam relay 71 where a small portion of the beam is extracted and provided to reference detector/monitor 73 to analyze the output in terms of optical intensities as well as passing on to processor 79 the tone frequency signals to be employed as reference frequencies in the employment of a lock-in amplifier technique at processor 79. Data analysis and control processor 79 provides or otherwise synthesizes the modulation tone frequencies to be applied to each pump laser 12 in laser array 60. These tone frequencies, as indicated previously, may be, for example, a first tone frequency below about or around 100 Hz and a second frequency above about or around 10 KHz; or a first frequency below about or around 100 Hz, a second frequency above about or around 10 KHz and a third frequency intermediate of these two frequency ranges such as around 1 KHz. There can be more than one such intermediate frequency and these tone frequency examples can be varied relative the maximum frequency response of fiber laser 14. The first frequency is below and the second frequency is above the maximum frequency response of any of the array fiber lasers 14. In the case of the third frequency, it is an intermediate frequency relative to the maximum frequency response and active relative to at least one rare earth fiber transition state of a rare earth species in the fiber core but not at other such transition states of any other present rare earth species. However, it is within the scope of this invention that such an intermediate frequency may activate more than one fiber rare earth transition state.

Returning now to FIG. 11, these modulation frequencies are provided to laser drive and control circuit 70 where the different sinusoidal modulation frequencies are provided to each laser 12 of hybrid lasers 60. Lasers 12 may operate at the same pumping wavelengths or may each operate at different pumping wavelengths depending upon the positions of the spectral characteristic features of the analyte under examination. Also, the modulation frequencies provided by circuit 70 to each laser 12 may be a plurality of the same modulation frequencies or may be different modulation frequencies, in either case, following the criteria, set forth above, i.e., one modulation frequency below and one above the maximum frequency response of the rare earth doped fiber lasers, and, in the case of a third or more frequencies, intermediate of the first two frequencies.

It should be understood that reference detector/monitor 73 may provide information to processor 79 as to the condition of the applied modulation frequencies in the output beam from hybrid laser array 60. Also, monitor 73 may also provide information about the intensity of the various wavelengths of radiation to laser drive and control circuit 70 in order to correct those intensities to desired levels by means of changing the current bias to pump lasers 12 in array 60.

After passage from beam splitter 72, the multi-wavelength, multi-frequency beam is relayed to specimen under test at 75 by means of beam relay 74. In the schematic illustration here, beam relay 71 is most generally a collimator of the diverging beam from the output of hybrid laser array 60 and beam relay 74 is most generally focusing optics to the analyte specimen at 75. The radiation beam reflected from or transmissive of the specimen is collected by beam relay 76 and provided to broadband laser detector/monitor 78 which may be comprised of a photodetector which detects the modulated radiation and provides a photocurrent replicating the multi-frequency modulations in the beam derived for the specimen under test or examination. The output of detector 78 is provided to data analysis and control processor 79 where the DC values of the various modulation frequencies are derived by a lock-in amplifier technique where the respective tone frequencies detected prior to specimen 75 from monitor 73 are multiplied by corresponding tone frequencies after specimen 75 from monitor 78 providing a plurality of DC values representative of the amplitude differences between identical tone frequencies, before and after specimen examination. Additionally the tone frequency pairs may have a phase difference, each of which value is a further quantity useful for the measurement of the amount of absorption by a specimen analyte at 75 at various wavelength spectral characteristic features along the absorption spectrum of the analyte.

A lock-in amplifier in processor 79 may also generate the plurality of tone frequencies employed for modulating each pump laser 12. The two sinusoidal frequencies of the reference signal and the specimen affect signal are multiplied together to obtain a DC amplitude value. If there is any difference in frequency between these two sinusoidal frequencies, the multiplied result will not be a DC value at zero frequency. However, multiplying the two frequency signals together which have the same frequency and phase relationship, a DC signal is produced that is twice the tone frequency. The signal is then passed through a low pass filter on the DC signal to obtain a narrow noise bandwidth and, therefore, improve the SNR to obtain a highly accurate amplitude value of the signal at a given tone frequency. Thus, a multiplication is being performed of the same tone frequency at both at the input to and at the output from the absorbent analyte at 75 from which a DC signal is obtained that is proportional to the amplitude value at a given absorption spectral feature.

The matrix multiplication mentioned above is actually a two step process. Photodetector 78 detects a set of N tone frequencies. Each of those N frequencies corresponds to N signals at N different wavelengths. So there is a first matrix multiplication to go from N tone frequencies to N amplitudes at N wavelengths. Then, there is a second matrix multiplication to go from N amplitudes at N wavelengths to determine the amount of concentration of the analyte in the specimen. The first matrix going from tone frequencies to wavelength intensities is reasonably deterministic. It is knowing what the frequency response curves are as well as knowing what the initially employed tone frequencies are. The second matrix is more difficult to determine the elements in the matrix because it involves an analysis of statistics relative to multiple factors starting with the effects that different human specimens will have on the tone frequency signals. With the right matrix, you multiply the amplitude of each of the frequency signals at different wavelengths by a weighted value to obtain the analyte concentration value.

If the values of the matrix points for the different amplitude sampled points across the absorption spectrum under examination are known, they are then multiplied by a predetermined weighted value determined by the above mentioned statistics, for each point and a final weighted average value of analyte concentration will be realized.

The relationship of the amplitude of the tone frequency signals at the multiple wavelengths both with and without the analyte absorbent characteristics affecting the signal provides a combination of amplitudes that map into the concentration of the analyte in the specimen under examination. This is a matrix multiplication where determining the DC amplitudes of the frequencies are weighted or multiplied by predetermined weighted values from which the amplitude or the amount of the analyte in the specimen is determined. In other words, the derived digital signal is actually tapped and multiplied by a weighted value and the multiple values are added and averaged. These amplitudes are all different for different spectral positions of wavelength spectral characteristic features in the absorption spectra of the analyte, depending also upon the amount of absorption at each given wavelength.

The information electronically obtained at multiple wavelength distinguishing spectral features along a portion of the analyte optical absorption spectrum provides a reliable measurement of the analyte concentration through multiple wavelength feature testing, comparison and measurement. It should be noted also that data analysis and control processor 79 is connected to laser drive and control circuit 70 to provide other information relative to operating characteristics of hybrid lasers 60 as will be explained in more detail relative to FIG. 12.

Figure 12:
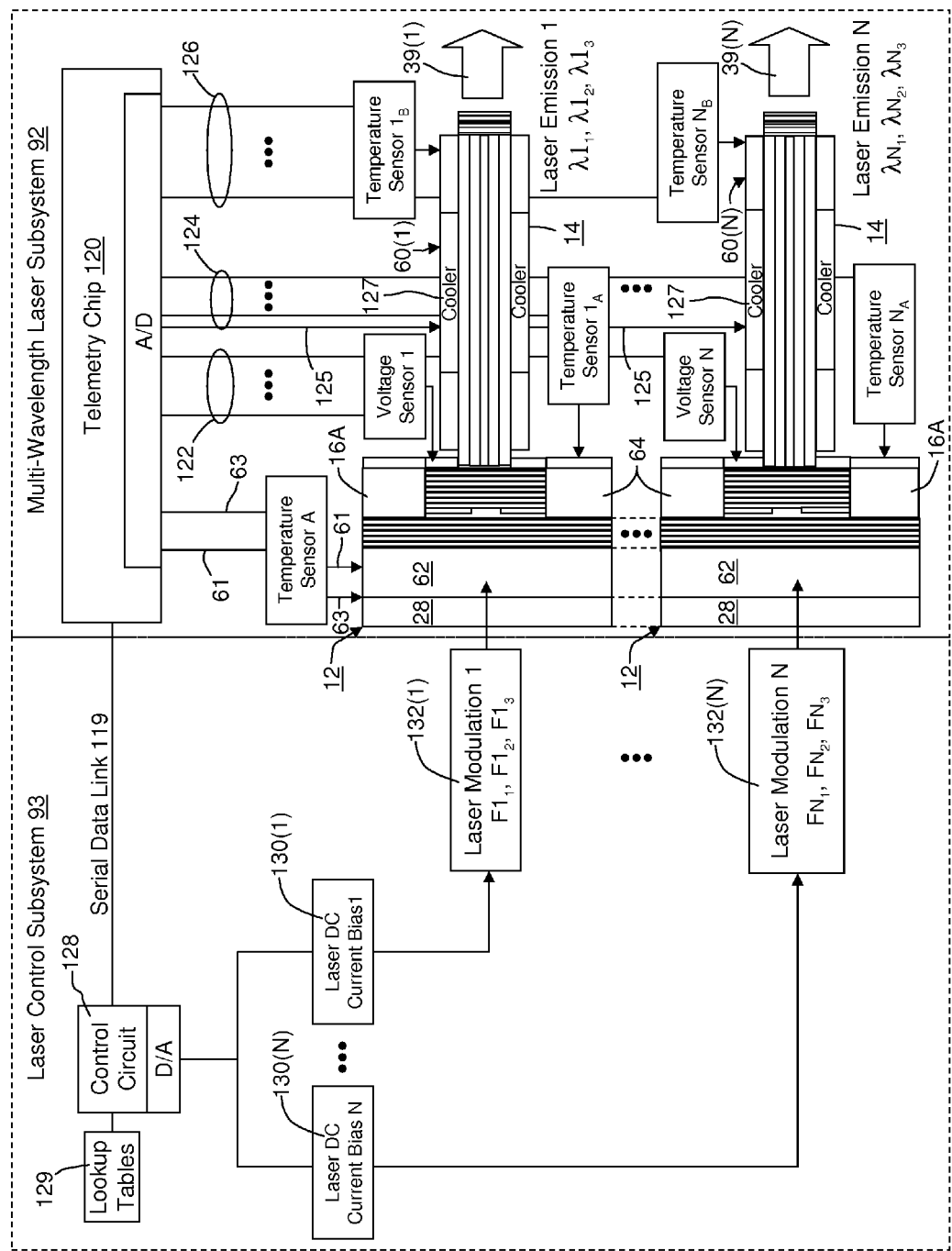
FIG. 12 is a schematic view of a first embodiment for subsystems that may be deployed in the systems of FIG. 10.

In FIG. 12, additional detail is disclosed relative to the multi-wavelength laser subsystem 92 and the laser control subsystem 93 of FIG. 10. N lasers 60(1) . . . 60(N) are formed on same substrate 62 with an accompanying heatsink 28. Relative multi-wavelength laser subsystem 92, temperature sensor, A, monitors the ambient temperature of the array substrate 62 via line 61 to telemetry chip 120. Such monitoring sensors are well known in the art and generally comprise a thermistor. It is also within the scope of this embodiment that temperature sensor may also include means to vary the temperature of substrate 62 such as, for example, by way of a strip heater (not shown) secured between 62 and heat sink 28 with current supplied to the heater via line 63 from telemetry chip 120. Also, each semiconductor laser 12 of hybrid lasers 60 may have a voltage sensor from 1 to N to monitor the voltage across the p-n junction of each pump laser 12. In addition, the local ambient temperature of each pump laser 12 may be monitored by a local temperature sensor $1_A$ to $N_A$ which are connected to telemetry chip 120 via lines 122. Sensors 1A to NA measure the temperature rise of each laser above the substrate temperature. The temperatures among lasers 12 vary because heat dissipation differs among these lasers. Further, the local ambient temperature of each rear earth fiber laser 14 of hybrid lasers 60(1) . . . 60(N) may be optionally monitored with temperature sensors $1_B$ to $N_B$ which are connected to telemetry chip 120 via lines 126. Thus, the electrical signals from these sensing devices are provided to telemetry chip 120 where lines 122 are inputs to chip 120 of the voltage drop sensor values 1 to N across each semiconductor laser 12, lines 124 are inputs of the local ambient temperature values $1_A$ to $N_A$ for each semiconductor laser 12, and lines 126 are inputs of the local ambient temperature values $1_B$ to $N_B$ for each rare earth fiber laser 14. Telemetry chip 120 is a digital signal processor (DSP) chip that takes as input a plurality of analog signals, digitizes them via an analog to digital (A/D) converter providing a series of data output at a given sampling rate that provide values representative of the voltage operation and local temperature of each semiconductor laser 12 as well as the local temperature of each fiber laser 14. This data is sent serially over a serial data link 119 to control circuit 128 in laser control subsystem 93. Thus, this data represents three digital values for each laser 60 for N such lasers 60(1) . . . 60(N) comprising the hybrid laser array. Since these analog signals do not change rapidly over time, a less expense serial link, rather than a parallel link, is sufficient as the sampling rate of these digital values may be, for example, in the ms range or even up to a second.

It is further within the scope of this disclosure that the operating temperature of fiber lasers 14 of hybrid lasers 60(1) . . . 60(N) may be varied or adjusted by means of thermoelectric coolers or other such Peltier type of coolers 127 as known in the art. Thermoelectric coolers (TECs) 127 operate by pumping heat toward or away from a surface of an element required to be temperature regulated employing the Peltier effect. This temperature control is of particular interest where the emission wavelengths of fiber lasers 14 are stable at a desired value where it is important to maintain precisely these emission wavelength wavelengths for particular analyte measurement applications. The temperature gradient in laser fibers 14 can affect the emission wavelength of one or more fiber laser optical outputs 39(1) . . . 39(N). The temperature of fiber lasers 14 are monitored by temperature sensors $1_B$ to $N_B$ and if any one of their temperature values significantly changes to be offset from a desired or predetermined emission wavelength of a given fiber laser 14, the desired operating temperature can be maintained via chip 120 and input lines 125 to any one of coolers 127 so that the corresponding fiber laser 14 operates precisely at desired emission wavelength or with a desired linewidth. In addition, it is within the scope of this disclosure that heaters (not shown) also be included in combination with coolers 127 attached to each fiber laser 14 to increase the dynamic range of temperature control of these lasers.

Alternatively, the information on the temperature of the individual fiber lasers may be used to deduce the emission wavelengths of the various lasers, and the algorithm for calculating species concentration may be adjusted to take into account thermal variations in the probing wavelengths. In this way, the additional cost of temperature control subsystems can be avoided.

In FIG. 12, further reference is now made to laser control subsystem 93 which comprises control circuit 128 with accompanying lookup tables 129. Output from control circuit 128 includes control signals provided to laser DC current bias 1 to N circuits 130(1) . . . 130(N) via a digital to analog (A/D) converter circuit which is part of circuit 128. The laser drive currents provided by circuits 130(1) . . . 130(N) are provide via laser modulation drive circuits 132(1) . . . 132(N) to pump lasers 12. Laser modulation drive circuits 132(1) . . . 132(N) perspective frequency modulation signals, $F1_1, F1_2, F1_3$, etc. to $FN_1, FN_2, FN_3$, etc., to pump lasers 12 along with the p-n junction current bias. The foregoing mentioned real-time digital values for lasers 12 or 14 from telemetry chip 120 are compared with values set for each such laser, such as derived during manufacturing testing, in lookup tables 129 which tables are accessed via control circuit 128. Based upon differences in values, the DC current bias of lasers 12 can be changed in order to change their output power level and also may be also deployed to increase the amplitude of the modulation current based upon reference information as to pump laser power levels and modulation amplitudes in lookup tables 129.

It may be asked why intensity monitoring of hybrid lasers 60(1) . . . 60(N) is not accomplished by taking a portion of output 93 from each later via a photodetector to determined laser power levels. The approach of FIG. 12 replaces the more expensive photodetectors with relative very inexpensive silicon IC circuitry and temperature sensors such as thermocouples, which can be fabricated in an integrated manner. Further, it is convenient in analyte testing not to interfere with the output beam path of hybrid lasers 60(1) . . . 60(N) and the intensity level of multiple lasers having multiple optical wavelength outputs, especially in testing situations where there is no ready access to the optical output path of these laser outputs.

Figure 13:
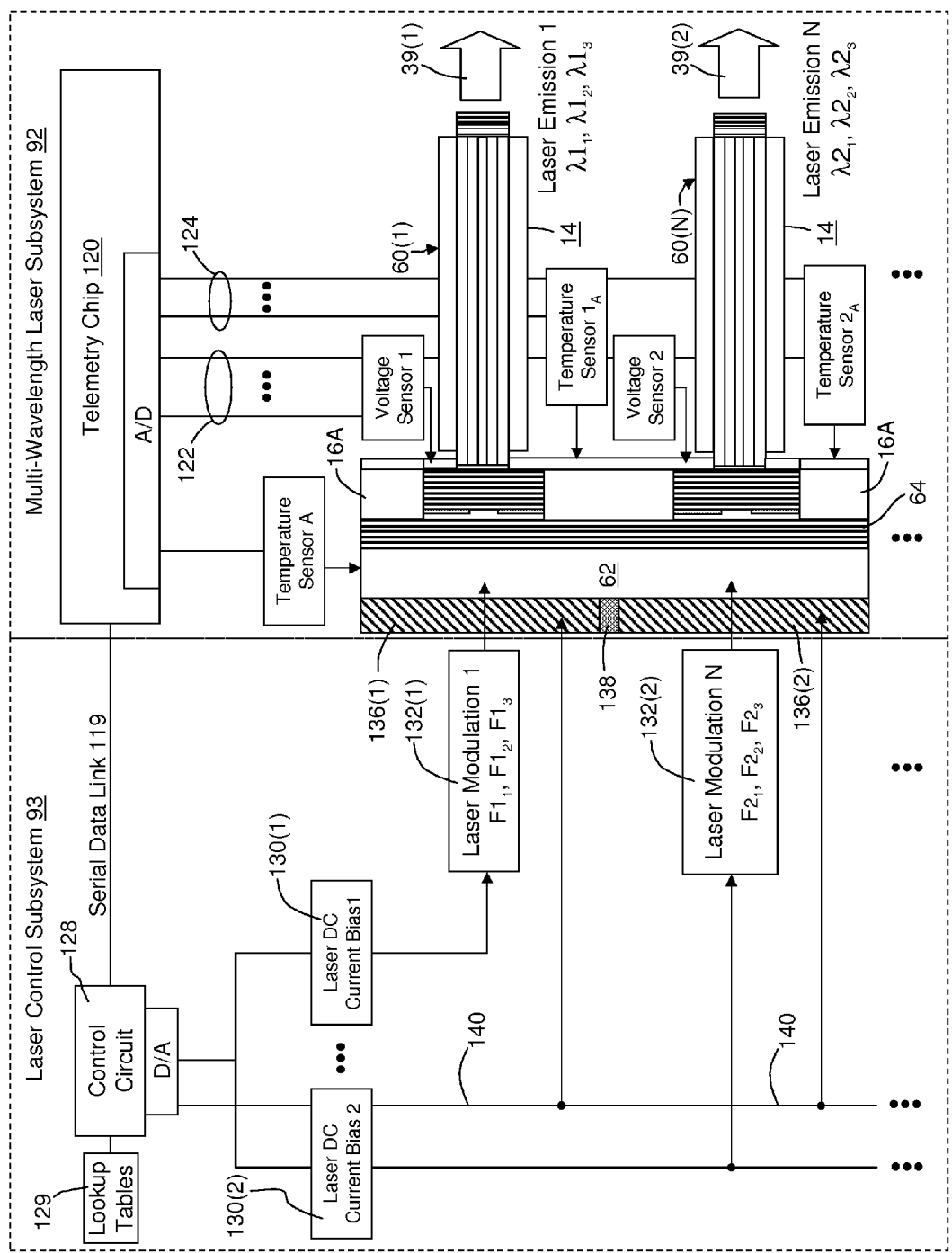
FIG. 13 is a schematic view of a second embodiment for subsystems that may be deployed in the systems of FIG. 10.

Reference is now made to FIG. 13 which is a modified version of the subsystems 92 and 93 shown FIG. 12. In FIG. 13, it is to be noted that, rather than utilizing heatsink 28, a plurality of micro-thermoelectric coolers (TECs) 136(1), 136(2), ... 136(N) or other type of Peltier micro-coolers are utilized to control the individual operating temperatures of each integrated semiconductor laser 12 for each hybrid laser 60(1), 60(2), ... 60(N). Each of the coolers 136 is thermally isolated from an adjacent cooler by means of a thermal isolator 138. In this embodiment, only the temperature of semiconductor pump lasers 12, as well as their junction voltages, are monitored via temperature sensors $1_A, 2_A, \ldots N_A$ and the monitored values are compared with predetermined values in lookup tables 129 to determine if a change is to be made to any one of these lasers relative to its corresponding cooler 136 via lines 140 provided to each of the coolers 136(1), 136(2), ... 136(N) as shown in FIG. 13.

Figure 16:
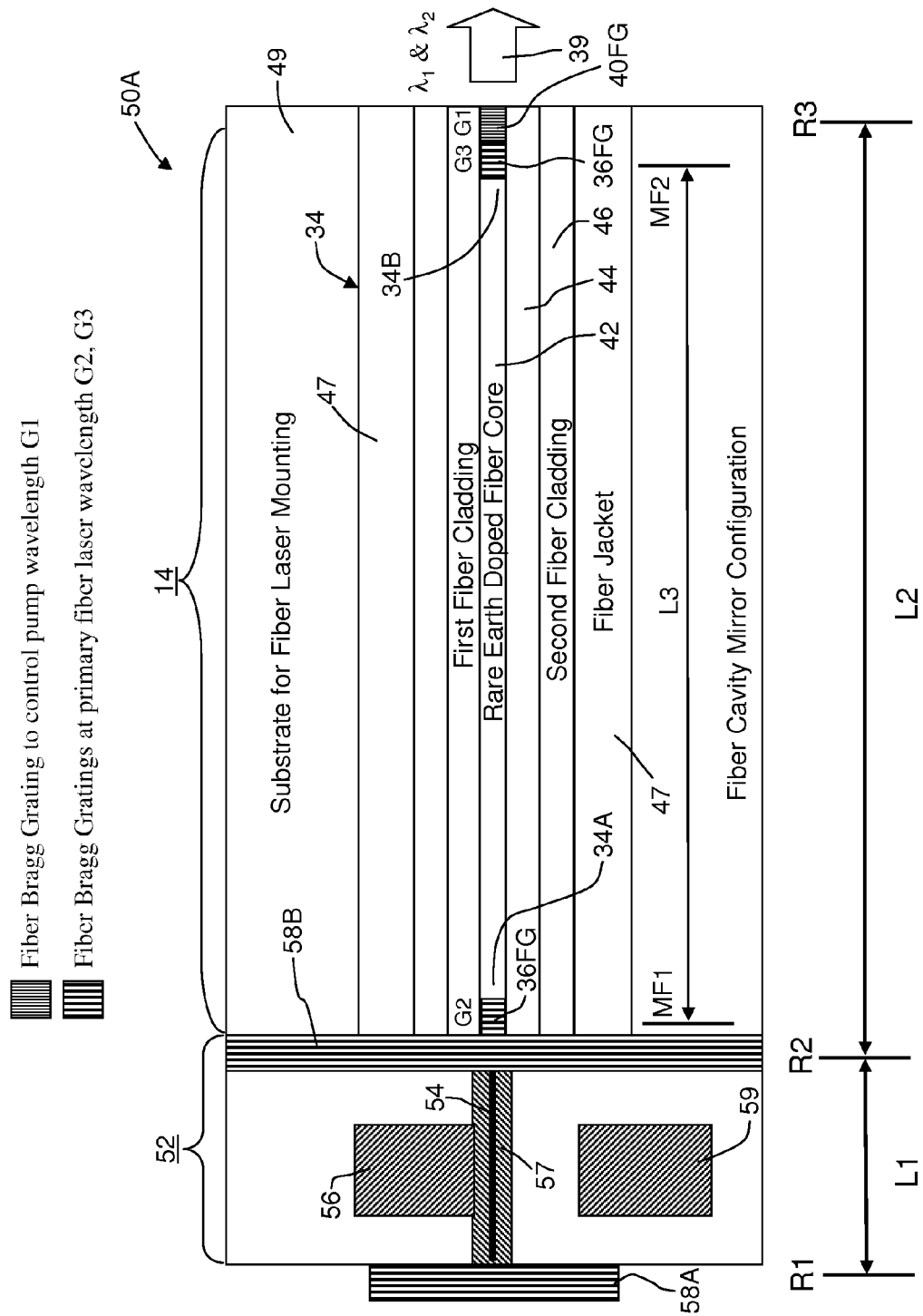
FIG. 16 is another embodiment of cross-sectional side elevation view of a side emitter pumped micro-fiber laser according to FIG. 2 having end-cavity fiber gratings forming a fiber laser cavity for deployment in this invention.

Reference is now made to FIG. 16 which primarily illustrates a multi-cavity laser 50A comprising a semiconductor laser for pumping a micro-cavity fiber laser which includes micro-cavity laser 14 butt coupled to semiconductor side emitter laser 52. Thus, the description of FIG. 2 is incorporated here by reference. Laser 50A thus is the same as laser 50 except that the laser 50A shown here includes fiber Bragg gratings 36FG and 40FG as cavity mirrors rather than deposited gratings to form the multiple lasing cavities that exist in laser 50A. Like numerical parts in FIG. 16 are the same as in FIG. 2 so that, as incorporated here, description of FIG. 2 equally applies to FIG. 16 for these parts. As true in connection with FIG. 2, laser 50A has two resonator cavities included in small cavity fiber laser 14, one cavity at the pump wavelength formed between grating 58A and front fiber Bragg grating 40FG at the out end of fiber laser 14 and a second cavity formed between front back fiber Bragg gratings 36FG. Fiber Bragg gratings 36FB and 40FB at the front or output end at beam 39 are set not to be fully reflective of cavity light at the resonating wavelengths of the two laser cavities so that these fiber gratings permit the extraction of them as output emission 39. To be noted is that micro-cavity fiber laser 14 is butt coupled to edge emitter laser 52. An edge emitter laser 52 is favored because it has potentially higher power relative to employing a VCSEL as a pump laser. However, it provides for reduced coupling efficiency with short cavity fiber laser 14 due to comparatively higher coupling losses, thus potentially favoring a VCSEL in applications with lower power requirements.

Fiber Bragg gratings or mirrors 36FG and 40FG are more favored than deposited cavity mirrors as illustrated in the previous embodiments because a greater degree of wavelength selectivity may be achieved. It is now possible to form gratings directly into monolithic fibers without the deployment of core dopants or hydrogen loading to bring about desired refractive index changes employing an UV beam either associated with a phase mask or using UV laser interferometry. However, fibers without such grating enabling dopants or hydrogen loading may be used in this disclosure, such as fluoride fibers with rear earth doped fluoride fiber cores incorporating, for example, $Tm^{3+}$ in a ZBLAN fiber. Other examples are $SiO_2$ fibers with Ge doped cores additionally incorporating a rare earth dopant such as $Tm^{3+}$. However one may choose to utilize more established UV methods in flouride fibers with the assistance of $Ce^{3+}$ as an activation agent as disclosed in {Poignant, 1994#304} these gratings can be preferred when compatibility with existing process lines and fabrication equipment is desired. See, for example, the article Poignant 1994 No. 304 It is, therefore, not required, as indicated above, to have hydrogen-loaded fibers or fibers that are doped to permit refractive index changes employing a diffraction mask and a UV laser or laser interferometry employing a UV laser. Instead, femtosecond pulsed infrared source with a phase mask or femtosecond pulsed laser interferometry is employed on such standard rare earth doped fibers to form the gratings, such as fiber gratings 36FG and 40FG in fiber laser 14 of FIG. 16. See, for example, Androz et al., "Monolithic fluoride-Fiber Laser at 1480 nm Using Fiber Bragg Gratings", *Optics Letters*, Vol. 32(10), pp. 1302-1304, May 15, 2007; Wikszak et al., "Erbium Fiber Laser Based on Intracore Femtosecond-Written Fiber Bragg Grating", *Optics Letters*, Vol. 31(16), pp. 2390-2392, Aug. 15, 2006; Mihailov et al., Bragg Gratings Written in All-$SiO_2$ and Ge-Doped Core Fibers With 800-nm Femtosecond Radiation and a Phase Mask", *Journal Of Lightwave Technology*, Vol. 22(1), pp. 94-100, January 2004; Smelser et al., "Generation of Pure Two-Beam Interference Grating Structures in an Optical Fiber With a Femtosecond infrared Source and a Phase Mask", *Optics Letters*, Vol. 29(15), pp. 1730-1732, Aug. 1, 2004; Oi et al., "Fabrication of Fiber Bragg Grating by Femtosecond Laser Interferometry", Proceedings, pp. 776-777, 2001; Bernier et al., "Bragg Gratings Photo-Induced in ZBLAN Fibers by Femtosecond Pulses at 800 nm, *Optics Letters*, Vol. 32(5), pp. 454-4456, Mar. 1, 2007; and U.S. Pat. Nos. 5,946,085; 6,993,221; 7,031,571; and 7,257,294, all of which articles and patents are incorporated herein by their reference. These femtosecond pulse-formed fiber grating processes may be applied equally to subsequent embodiments to be discussed later.

Figure 17:
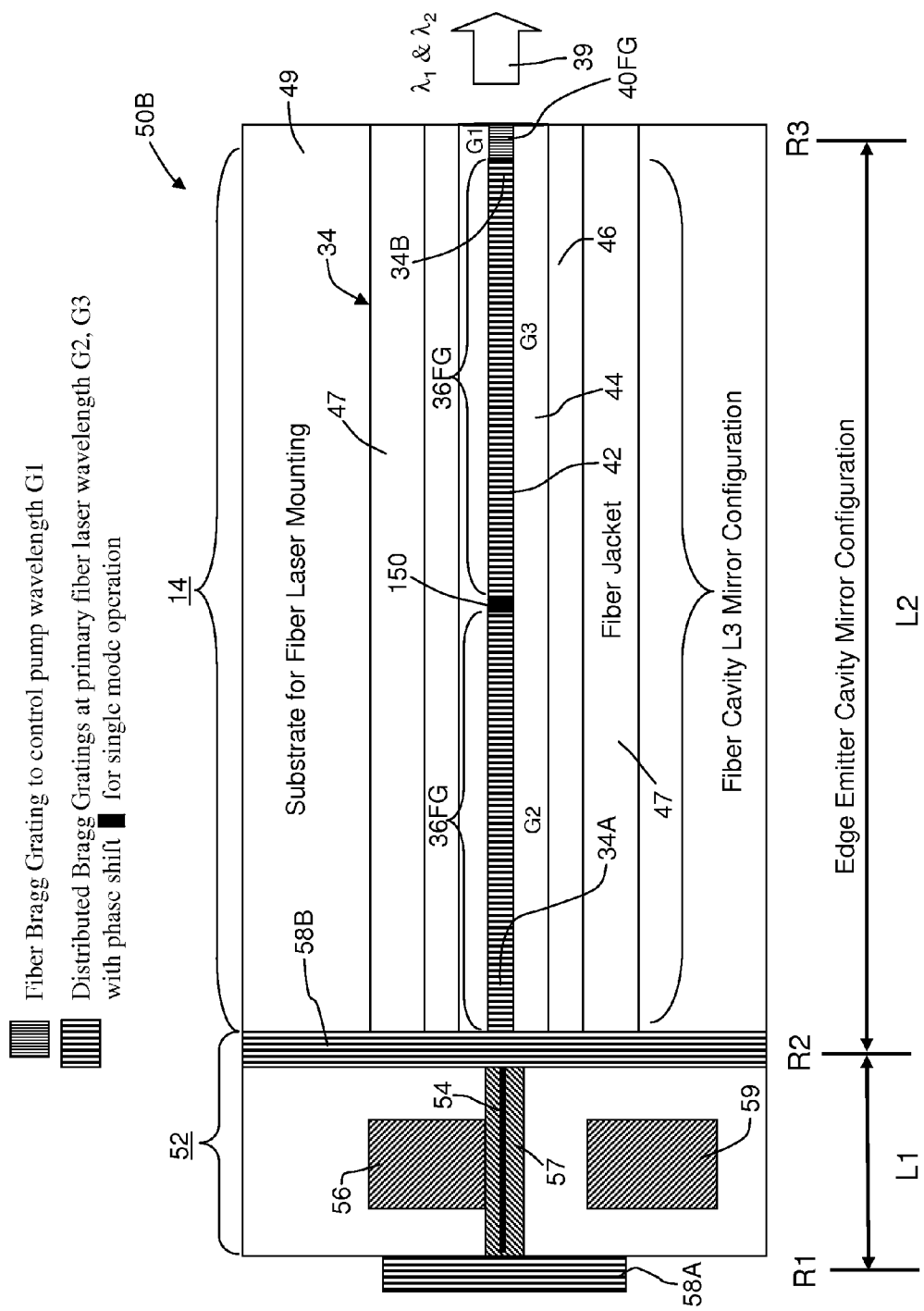
FIG. 17 is another embodiment of cross-sectional side elevation view of a side emitter pumped micro fiber laser according to FIG. 2 having cavity fiber gratings, similar to a distributed feedback laser (DFB) cavity, forming a fiber laser cavity for deployment in this invention.

FIG. 17 discloses multi-cavity hybrid laser 50B which is similar to laser 50A of FIG. 16 except that the fiber gratings 36FG extend through the cavity of fiber laser 14 with a phase shift 150 provided between the two gratings. Thus, fiber gratings 36FG function as distributed feedback (DFB) fiber laser. This structure in FIG. 17 thus effectively distributes the reflectivity of fiber gratings G2 and G3 (36FG) throughout the length of the fiber laser cavity L3 and enhances the ability of laser 50B to perform in a single longitudinal mode.

Figure 18:
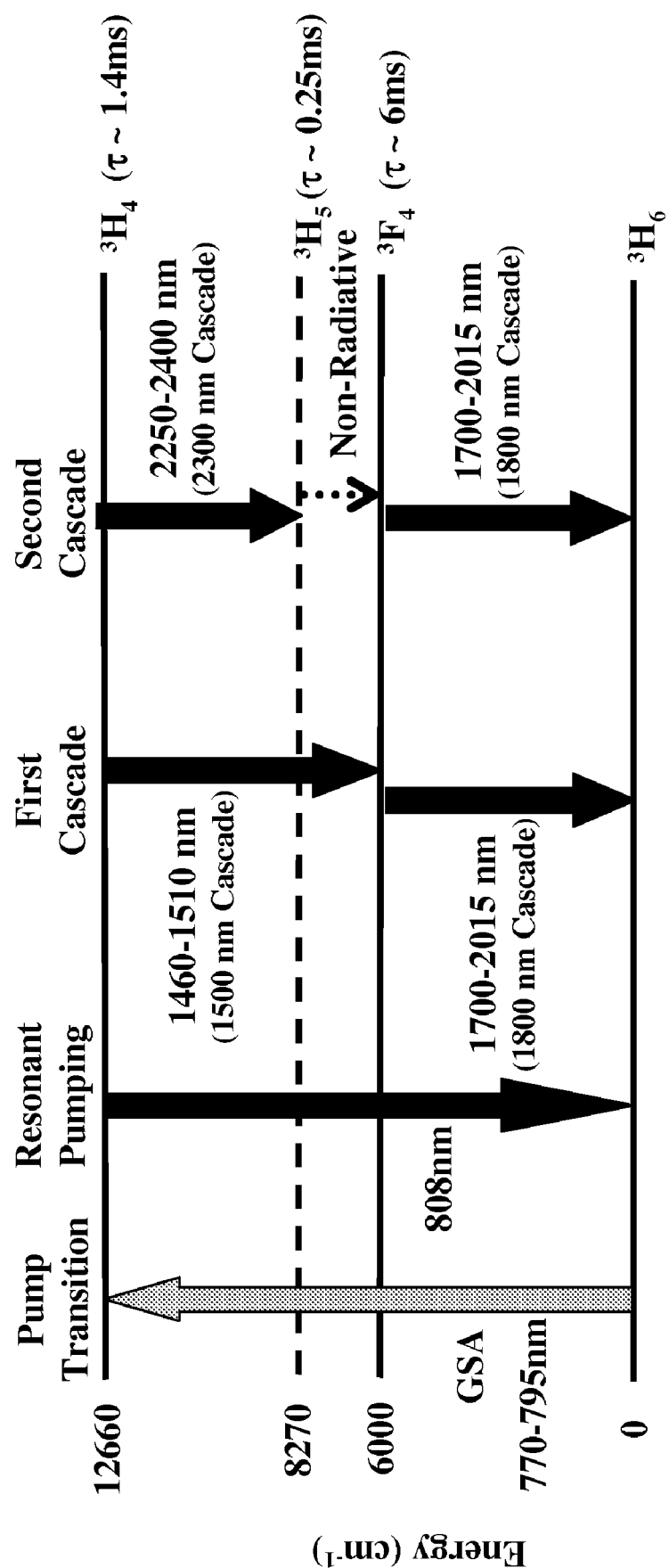
FIG. 18 is a further detailed energy-level transition diagram for thulium.

FIG. 18 is a more detailed energy-level transition diagram for thulium illustrating efficiency improvement by the use of multiple wavelength cascades. The cascade laser process involves increasing the rate at which electrons transition downwards from the pump transition excited state back down to the ground state by providing for stimulated emission (i.e. lasing) on as many as possible, if not all, of the energy level transitions that the electron must undergo. Further details of the operation of cascade lasers may be found in the articles of Schneider, "Mid-Infrared Fluoride Fiber Lasers in Multiple Cascade Operation", *IEEE Photonics Technology Letters*, Vol. 7(4), pp. 354-356, April 1995, and Percival et al., "Highly Efficient CW Cascade Operation of 1.47 and 1.82 mm Transitions in Tm-Doped Fluoride Fiber Laser", *Electronic Letters*, Vol. 28(20), pp. 1866-1868, 24 Sep. 1992, both of which are incorporated herein by their reference. Several different cascade laser schemes enable efficient photon extraction of cascaded photons when pumped with a pump source 52 in the range of 770 nm to 795 nm. Rear earth doped core fiber lasers of the cascade variety, as, for example, shown at first and second cascade in FIG. 18, can be realized with lasing at two wavelengths simultaneously such as illustrated in the first cascade or the second cascade in FIG. 18. These cascaded lasers result in high efficiency due to rapid depopulation of the terminal laser level. Note, however, that such cascade operation necessitates a second pair of grating mirrors in order to establish a third resonator cavity, the three resonator cavities comprising the composite pump resonator cavity L1 plus L2 and two fiber resonator cavities in L2 as seen in FIG. 19.

Figure 19:
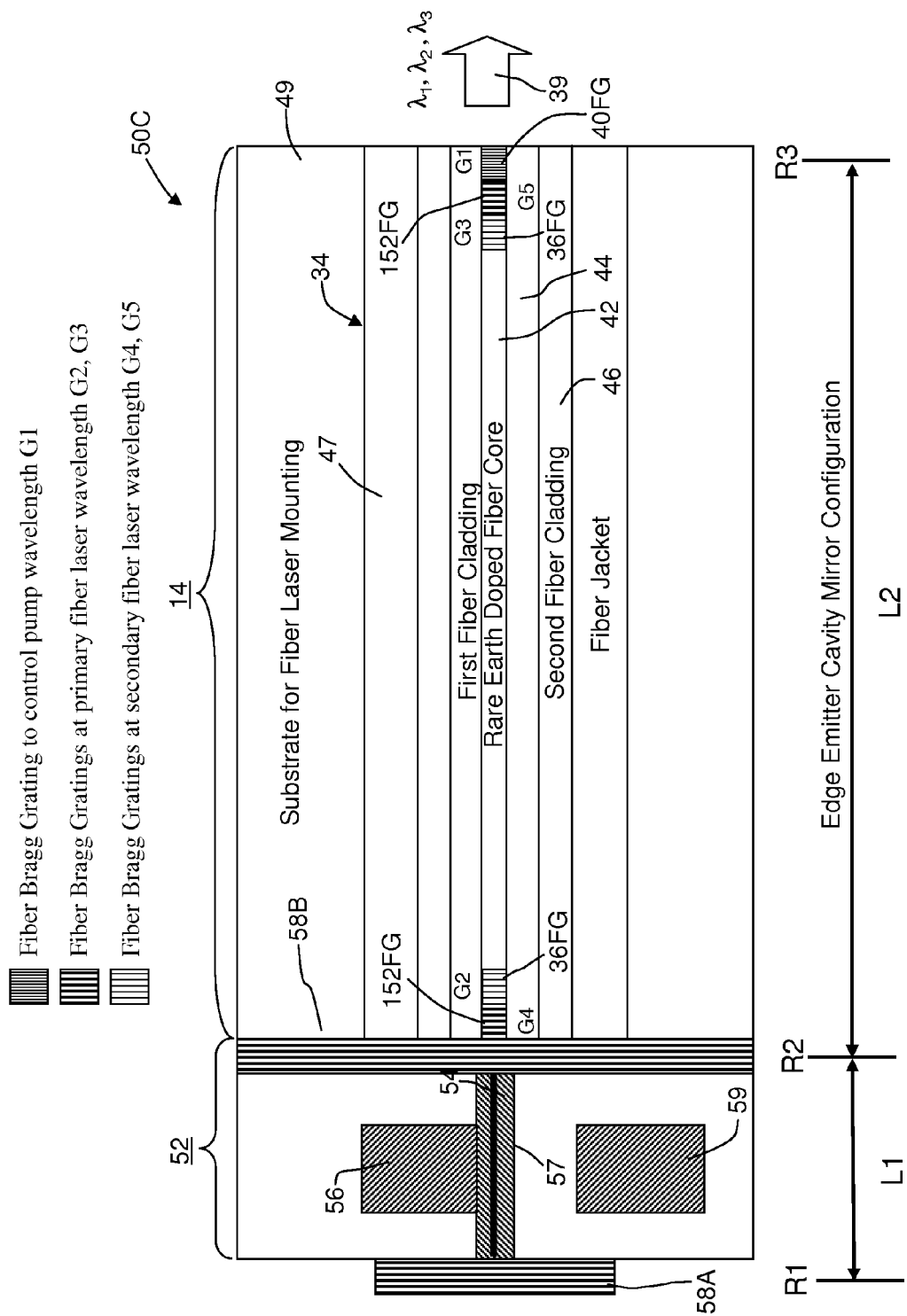
FIG. 19 is a further embodiment of cross-sectional side elevation view of a side emitter pumped micro fiber laser according to FIG. 2 having multiple end-cavity fiber gratings forming a plurality fiber laser cavities for deployment in this invention.

In FIG. 19, a pair of fiber Bragg gratings 152FG are include with the pair of fiber Bragg gratings 36FG, previously introduced in FIG. 16, to form the second fiber laser resonator between gratings 152FG operating at an emission wavelength of the doped optical fiber 34. As an example, relative to the first cascade in FIG. 18, the 36FG formed cavity can operate at an emission wavelengths of 1500 nm and the 152FG formed cavity can operate at 1800 nm. A first benefit realized here is that now two fiber laser wavelengths become available in output emission 39. A second benefit realized is that laser power saturation effects and self-terminating effects can be eliminated by providing for faster depopulation of the terminal lasing level via stimulated emission when the terminal level has too long a lifetime. In such cases, electrons will tend to "pile up" in the terminal level creating a bottleneck which will reduce the lasing efficiency or, in extreme cases extinguish the laser emission completely, a so-called self-terminating laser condition. The multiple cavity laser of FIG. 19, thus, has three resonator cavities that include cavity L2, one at the pump wavelength and two at the pair of fiber laser emission wavelengths formed by fiber grating pairs 36FG and 152FG and the output fiber gratings 36FG, 40FG and 152FG permit the extraction of three wavelengths of emission at 39.

Figure 20:
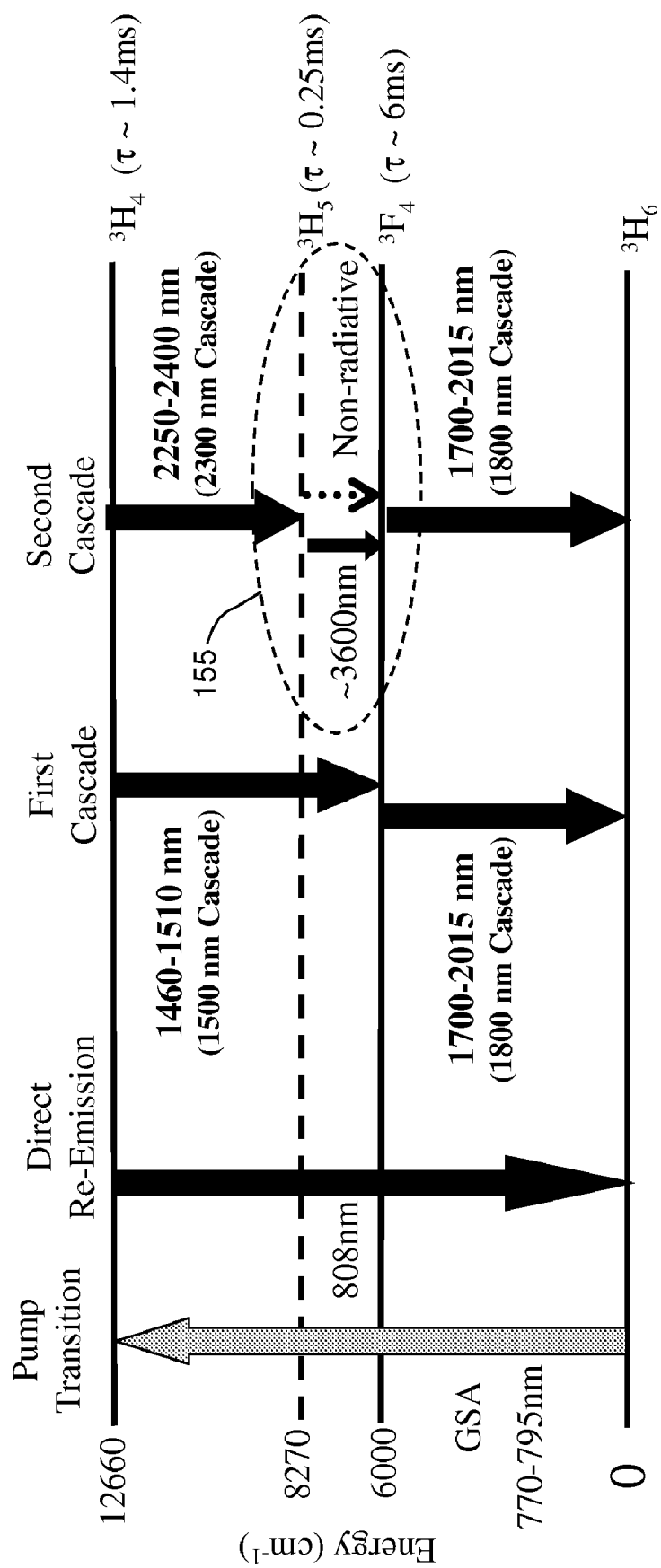
FIG. 20 is a still further detailed energy-level transition diagram for thulium illustrating multiple cascade transitions where efficient photon extraction can occur.

FIG. 20 is a further detailed energy-level transition diagram for thulium showing the multiphonon non-radiative combination at 155 in the second or 2300 nm cascade for thulium. Conventional 2300 nm cascade laser devices rely on the third, approximately 3600 nm cascade non-radiative multiphonon transitions to depopulate the $^3H_5$ level. Reliance on multiphonon relaxation from $^3H_5$ to $^3F_4$ results in "phonon relaxation bottleneck", which can be relieved by providing a parallel path for relaxation via photon-assisted stimulated relaxation, which becomes more rapid with higher photon density. This allows for higher photon emission rates in the overall cascade system. Thus, this depopulation becomes a bottleneck at high laser power density. There is a benefit to constructing a third cascade 155 at 3600 nm point, in the second cascade that includes the 2300 nm cascade and the 1800 cascade, in order to provide a more rapid stimulated emission driven depopulation of the $^3H_5$ level than can be realized by multiphonon emission alone. This third level emission in the second cascade at the 3600 nm wavelength has many useful applications including optical spectroscopy apparatus for determining the concentration of analyte in a specimen as disclosed herein.

Figure 21:
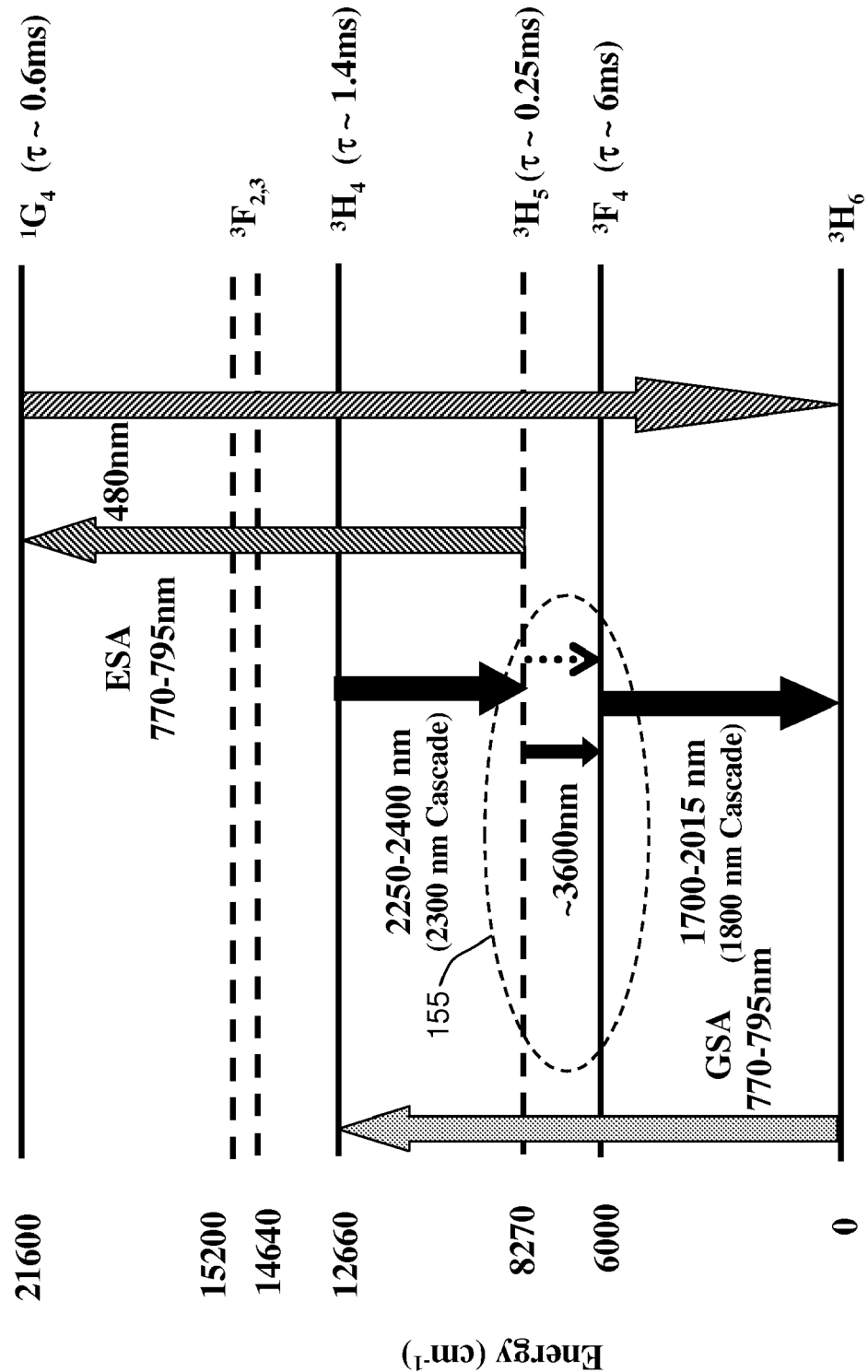
FIG. 21 is an expanded energy-level transition diagram for thulium relative to the second cascade transition.

FIG. 21 is an expanded energy diagram for thulium showing absorption and emission within the thulium atom when operated in the second cascade. It is reported that there is rollover at high power in a 2300 nm cascaded laser. The rollover results from the very high electron flux from the $^3H_5$ to the $3F_4$ levels as the total output power increases. This total fux becomes greater than what can be accommodated for by the fixed multi-photon relaxation rate, and thus becomes the rate limiting (and therefore power limiting) step in the cascade process. See Caspary,. "Applied Rare Earth Spectroscopy for Fiber Laser Optimization" Berichte aus der Lasertechnik. Aachen: Shaker (2002)., incorporated herein by its reference. The reason why is electron decay due to the fast buildup of electrons in the $^3H_5$ level but not fast enough. One signature of excess electron buildup in the $^3H_5$ level is that electrons in this level may undergo excited state absorption into the $^1G_4$ level. From this level they may undergo spontaneous emission back down to the ground state, emitting a blue photon in the process. It has been recognized also that there is blue wavelength light emission as well as rollover. See Percival et al, "Highly Efficient CW Cascade Operation of 1.47 and 1.82 µm Transitions in Tm-Doped Fluoride Fiber Laser", *Electronic Letters*, Vol. 28(20), pp. 1866-1868, Sep. 24, 1982, previously incorporated herein by reference. The enhanced blue emission is due to excited state absorption (ESA) from the electron buildup in the $^3H_5$ level, as shown in FIG. 21, which competes with the desired cascade cycle. Reducing lifetime at the $^3H_5$ level can be accomplished by encouraging stimulated emission at 3600 nm which will also improve the power available and efficiency at the 2300 nm and the 1800 nm emission wavelengths of the cascade. Thus, what results is a tri-resonant cavity fiber laser 50D which is illustrated in FIG. 22.

Figure 22:
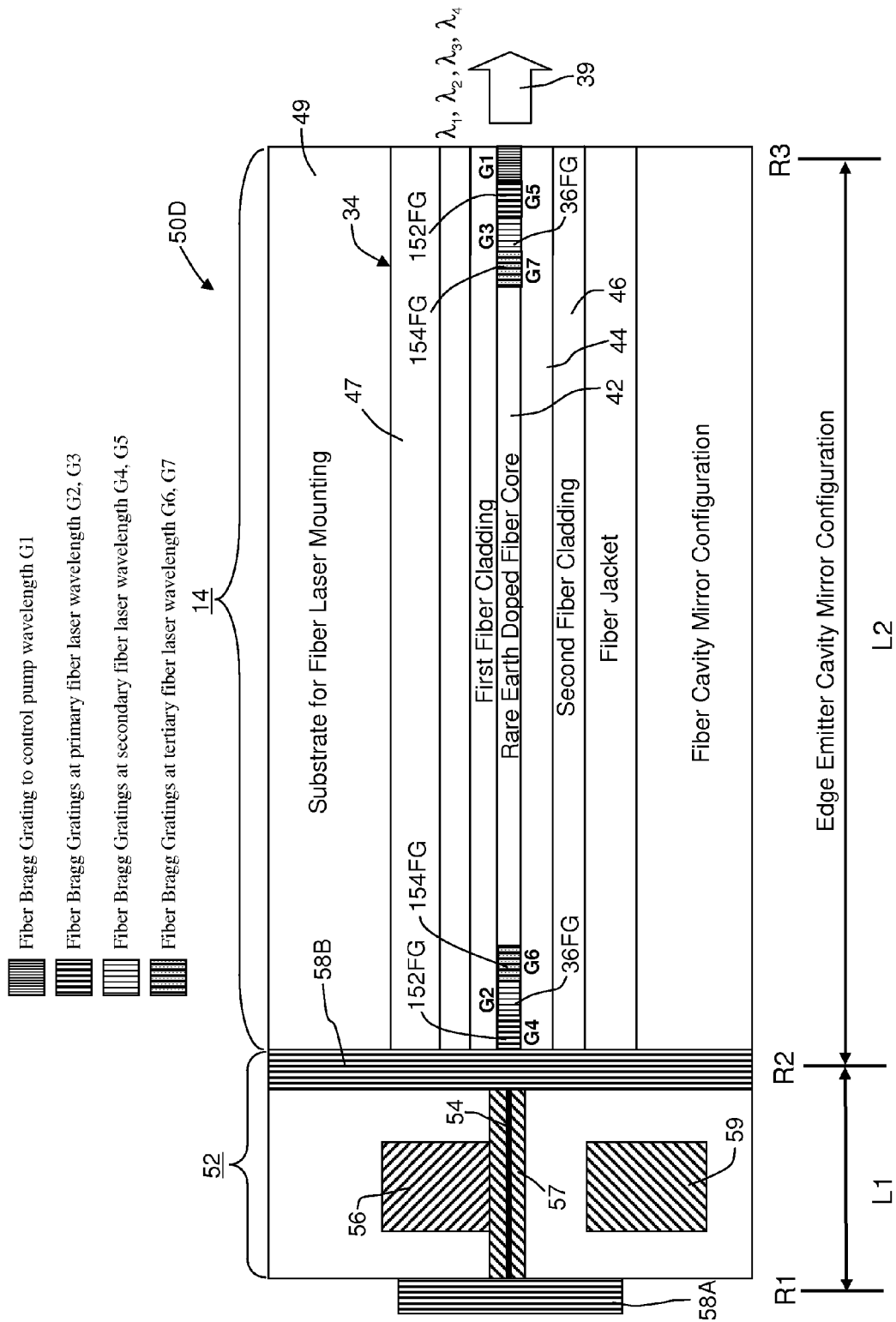
FIG. 22 is a further embodiment of cross-sectional side elevation view of a side emitter pumped micro fiber laser according to FIG. 19 having further multiple end-cavity fiber gratings forming a plurality of fiber laser cavities (three fiber laser cavities) for deployment in this invention.

The embodiment of FIG. 22 is the same as the FIG. 19 embodiment except carries an additional pair of fiber Bragg gratings 154FG. As illustrated in FIG. 22, additional fiber Bragg gratings 154FG are incorporated into the tri-resonator cavity fiber laser 14 to fabricate a third emission wavelength in the 3600 nm cascade in the doped fiber 34. The other two pairs of fiber Bragg gratings 36F and 152FG are set to wavelengths in the 2300 nm cascade and the 1800 nm cascade of the identified second cascade. Thus, a trio of fiber laser wavelengths may be extracted at the emission output 39 along with a fourth wavelength at the pump wavelength. An important benefit too is that power saturation effects and self-terminating effects can be eliminated by providing for faster depopulation of multiple terminal lasing levels via stimulated emission. The overall result is higher output powers available for all of the participant wavelengths in the cascade. The four wavelengths, selected by the grating mirrors for emission at emission output 39 can be designed to be at substantially matched to four distinguishing spectral characteristic features along at least a portion of an characteristic optical spectrum of the analyte under examination.

While the invention has been described in conjunction with several specific embodiments, it is evident to those skilled in the art that many further alternatives, modifications and variations will be apparent in light of the foregoing description. While the approach of this invention has been exemplified mostly in regard to analytes involving living tissue, it will be understood by those skilled in the art that the principals of this invention herein may be utilized in examining other specimens that may not include living tissue specimens where multi-frequency outputs of optical signals may be employed for statistical examination, such as, for example, LIDAR, atmospheric gas sensing, environmental monitoring and atomic/molecular spectroscopy in general. Within this context, an analyte may be an atom or molecule in the vapor phase, and a specimen may be a free space path between a laser and a detector containing some concentration of the vapor phase analyte. Thus, the invention described herein is intended to embrace all such alternatives, modifications, applications and variations as may fall within the spirit and scope of the appended claims.

What is claimed is:

1. A method of determining the concentration of an analyte in a specimen comprising the steps of:
providing a hybrid laser that comprises a first and second laser for producing at a single output a plurality of emission wavelengths that substantially match distinguishing wavelength spectral characteristic features along at least a portion of a characteristic optical spectrum of the analyte;
modulating the first laser with a plurality of tone frequencies where at least one of said tone frequencies is above a maximum frequency response of the second laser so that at least one emission wavelength from the second laser is not modulated by a tone frequency;
applying the modulated output emission wavelengths to the specimen under examination;
detecting radiation reflected, scattered or passed through the specimen;

producing a set of values representative of wavelength spectral characteristic features of the analyte within the characteristic optical spectrum portion from the applied modulated output emission wavelengths and the detected reflected radiation; and determining the differences in the produced set of values with predetermined reference values representative of desired wavelength spectral characteristic features of the analyte to produce a final value representative of a measurement of concentration of the analyte in the specimen.

2. The method of claim 1 wherein the wavelength spectral characteristic features are amplitude absorption values at the absorption peaks along at least a portion of a characteristic optical spectrum of the analyte.

3. The method of claim 1 wherein the step of determining includes the steps of:

multiplying each of the set of values with a weighted value; and thereafter average the weighted values to produce a final value representative of a measurement of concentration of the analyte in the specimen.

4. The method of claim 1 comprising the further step of providing the first laser to be a semiconductor laser and the second laser to be a fiber laser.

5. The method of claim 1 comprising the further step of modulating the hybrid laser with a plurality of tone frequencies.

6. The method of claim 1 comprising the step of providing the first laser to have an emission wavelength to pump the second laser.

7. The method of claim 1 comprising the further step of providing one of the emission wavelengths in the hybrid laser output to be an emission wavelength of the first laser.

8. The method of claim 1 comprising the further step of providing the second laser to have a maximum frequency response below that of the first laser; and applying tone frequencies to modulate the hybrid laser where at least one of the tone frequencies is non-responsive to modulating at least one of the emission wavelengths from the second laser.

9. The method of claim 1 comprising the further step of providing one of the emission wavelengths in the hybrid laser output to be an emission wavelength of the first laser.

10. An optical spectroscopy apparatus for determining the concentration of analyte in a specimen that utilizes a radiation source comprising at least one combination of a semiconductor pump laser and small-cavity fiber laser where laser cavities of both lasers are butt coupled to provide a plurality of laser resonant cavities where the cavities are all, at least in part, formed by fiber Bragg gratings formed in the core of the laser fiber that produce a plurality of emission wavelengths at a same output of the butt coupled laser that are designed to substantially match distinguishing spectral characteristic features along at least a portion of a characteristic optical spectrum of the analyte under determination.

11. The optical spectroscopy apparatus of claim 10 wherein the fiber laser comprises a rare earth doped fiber wherein the fiber Bragg gratings are formed near or at the fiber ends employing a femtosecond pulsed infrared laser process.

12. A multi-cavity laser having a multi-wavelength output at one end, comprising a semiconductor pump laser optically coupled to a short cavity fiber laser having a rare earth doped core, the multi-cavity laser having a first resonator cavity formed by the laser cavities of the semiconductor laser and the fiber laser via a first mirror at one end of the semiconductor laser cavity and a mirror at the one end and at least one second resonator cavity formed in the fiber laser cavity with, respectively, a second and third mirror at each end of the fiber lasing cavity forming the second resonator cavity, the first, second and third mirrors formed as fiber Bragg gratings in the rare earth doped core.

13. The multi-cavity laser of claim 12 wherein the doped fiber core of the short cavity fiber laser provides for at least two cascaded transitions where the second and third mirrors as well as fourth and fifth mirrors also at or near the ends of the fiber laser cavity provide at the multiwavelength output two wavelengths generated from a two-step cascade transition.

14. The multi-cavity laser of claim 13 further comprising a third wavelength is provided at the output at a wavelength of the semiconductor pump laser.

15. The multi-cavity laser of claim 13 further comprising a third wavelength provided at a nonradiative multiphonon transition in the two-step two cascaded transition.

* * * * *